United States Patent [19]

Nakahama et al.

[11] Patent Number: 5,182,195
[45] Date of Patent: Jan. 26, 1993

[54] METHOD FOR INCREASING GENE EXPRESSION USING PROTEASE DEFICIENT YEASTS

[75] Inventors: Kazuo Nakahama, Nagaokakyo; Yoshihiko Kaisho, Sakai; Koji Yoshimura, Osaka, all of Japan

[73] Assignee: Takeda Chemical Industries, Ltd., Osaka, Japan

[21] Appl. No.: 269,140

[22] Filed: Nov. 9, 1988

[30] Foreign Application Priority Data

Nov. 13, 1987 [JP] Japan .................. 62-285175

[51] Int. Cl.$^5$ .................. C12N 1/19; C12P 21/02
[52] U.S. Cl. .................. 435/69.1; 435/255; 435/942; 935/69
[58] Field of Search .................. 435/69.1, 255, 942; 935/41, 69

[56] References Cited

U.S. PATENT DOCUMENTS

| | | | |
|---|---|---|---|
| 4,752,576 | 6/1988 | Brake et al. | 435/69.1 |
| 4,766,068 | 8/1988 | Oeda et al. | 435/69.1 |
| 4,945,051 | 7/1990 | Kikuchi et al. | 435/172.3 |
| 4,983,520 | 1/1991 | Yukio et al. | 435/69.3 |

FOREIGN PATENT DOCUMENTS

| | | |
|---|---|---|
| 0171908 | 3/1985 | European Pat. Off. |
| 0181634 | 11/1985 | European Pat. Off. |
| 0175283 | 12/1985 | European Pat. Off. |
| 0177915 | 4/1986 | European Pat. Off. |
| 0235430 | 8/1986 | European Pat. Off. |
| 8703298 | 4/1987 | PCT Int'l Appl. |

OTHER PUBLICATIONS

Sagata et al. Nature 335 (1988) 519-525.
Brake et al. PNAS vol. 81, pp. 4642-4646 1984.
Sherman et al. Cold Spring Harbor Laboratory 1986.
Gunge & Yamane, J. Bact. 159, 533-359 (1984) Incompatibilty of Linear DNA Killer Plasmids pGKL1 and pGKL2 from Kluyveromyces ...
V. Parikh, et al, Science 235:576-580 (1987) The Mitochondrial Genotype Can Influence Nuclear Gene Expression in Yeast.
Harashima et al., Molecular and Cellular Biology, vol. 4, No. 4, Apr. 1984, pp. 771-778.

Primary Examiner—Richard A. Schwartz
Assistant Examiner—John LeGuyader
Attorney, Agent, or Firm—David G. Conlin; Linda M. Buckley

[57] ABSTRACT

Disclosed are respiratory-deficient yeast except Saccharomyces cerevisiae AH22R$^-$, said respiratory-deficient yeast being transformed with a DNA containing a gene encoding a protein foreign to yeast and a method for preparing a protein foreign to yeast described above, which comprises culturing the yeast, and producing and accumulating the protein in a culture. The respiratory-deficient yeast of the present invention can produce a higher amount of protein than its parent strain.

7 Claims, 22 Drawing Sheets

TaqI
TCGAGAGATGCGAATTAGCCAGAACTTTGAAGAGATTGGGTATGGACGGCTACCGTGGTATTTC
AGCTCTCTACGCTTAATCGGTCTTGAAACTTCTCTAACCCATACCTGCCGATGGCACCATAAAG

HpaII        MaeIAluI
TTTAGCCAACTGGATGTGTCTTGCTAAGTGGGAATCCGGCTATAACACTAGAGCTACCAATTAC
AAATCGGTTGACCTACACAGAACGATTCACCCTTAGGCCGATATTGTGATCTCGATGGTTAATG

Xbal
AACGCTGGCGACCGTTCTACAGACTATGGTATTTTCCAAATTAACTCTAGATATTGGTGTAACG
TTGCGACCGCTGGCAAGATGTCTGATACCATAAAAGGTTTAATTGAGATCTATAACCACATTGC AluI
ATGGCAAGACTCCAGGTGCCGTCAACGCCTGTCACTTATCTTGCTCAGCTTTGCTTCAGGACAA
TACCGTTCTGAGGTCCACGGCAGTTGCGGACAGTGAATAGAACGAGTCGAAACGAAGTCCTGTT HhaI
CATTGCTGATGCTGTTGCCTGCGCTAAGAGAGTTGTCCGTGACCCACAGGGTATTAGAGCCTGG
GTAACGACTACGACAACGGACGCGATTCTCTCAACAGGCACTGGGTGTCCCATAATCTCGGACC GTCGCTTGGAGAAACAGATGCCAAAATAGAGATGTCAGACAATACGTTCAAGGTTGTGGTGTTT
CAGCGAACCTCTTTGTCTACGGTTTTATCTCTACAGTCTGTTATGCAAGTTCCAACACCACAAA XhoI
  AluI
AATAGCTCGA
TTATCGAGCT

```
XhoI           M  R  S  F  L  L  L  A  L  C  F  L  P  L  A  A  L  G           TaqI
 |___          |___                      |___                      |___
   #1            #3                        #5                        #7
TCGAGTATAAAAACAATGAGATCTTTCTTGTTGTTGGCTTTGTTCTTGCCATTGGCTGCTTTGGGTAAGGTTTT
     CATATTTTGTTACTCTAGAAGAAGAACAACCGAAACAAGAACGGTAACCGACGAAACCCATTCCAAAAGC
     |___                      |___                      |___
       #2                        #4                        #6                        #8
```

FIG. 8

```
5'
GATCACCGCGGATCCGGTTACCGTCGACTATAATGACAGATC
TGGCGCCTAGGCCAATGGCAGCTGATATTACTGTCTAGAGCT
                                          3'
```

FIG. 11

```
XhoI           M  R  S  L  L  I  L  V  L  C  F  L  P  L  A  A  L  G  K  V  S
 |___          |___                      |___                      |___
   #1            #3                        #5                        #7
TCGAGTATAAAAACAATGAGATCTTTTGTTGATCTTGTTGTTTGTTCTTGCCATTGGCTGCTTTGGGTAAGGTTAGC
     CATATTTTGTTACTCTAGAAACAACTAGAACCAAAACACAAAGAACACAAAGAACGGTAACCGACGAAACCCATTCCAAT
     |___                      |___                      |___
       #2                        #4                        #6                        #8
```

XhoI  M R S F L L L A L C F L P L A A L G N S D
TCGAGTATAAAAACAATGAGATCTTTCTTGTTGTTGGCTTTGTGTTTCTTGCCATTGGCTGCCCTAGGTAACAGTG
CATATTTTTGTTACTCTAGAAAGAACAACAACCGAAACACAAAGAACGGTAACCGACGGGATCCATTGTCACTAA
HinfI
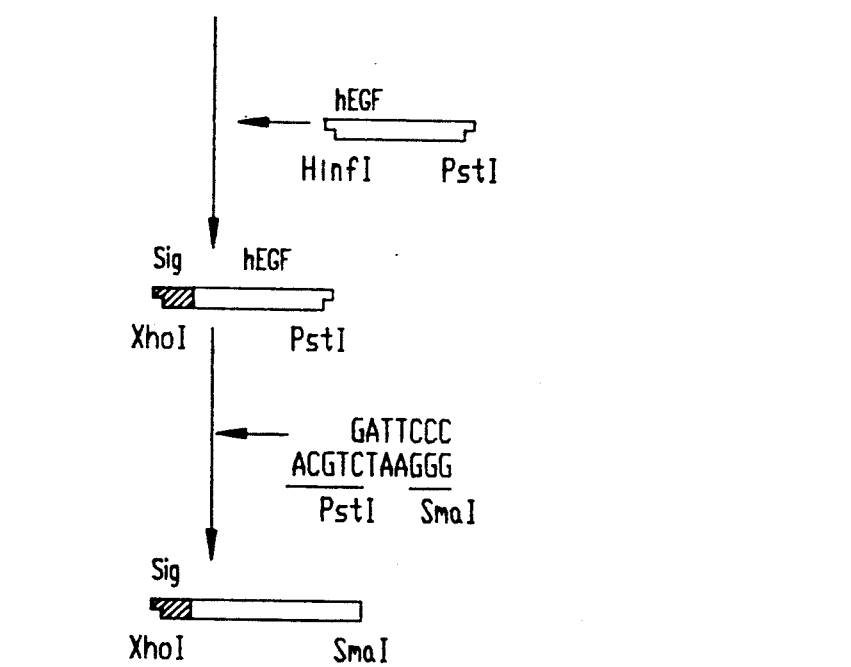
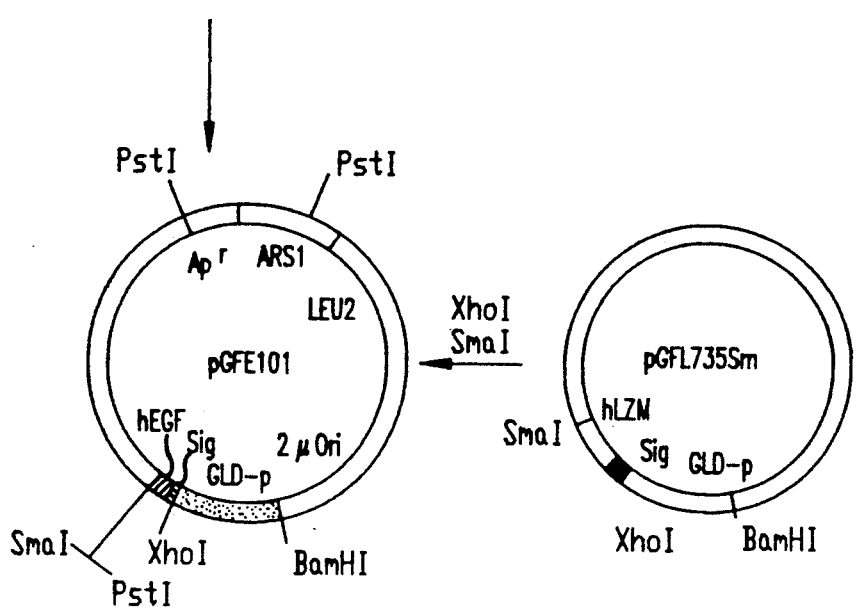
FIG.7

```
   1  TTT AAA AAG CAG GGG TTA GGG AGT TGT TCG GTC ATA AGC TTC AGC
  46  GCG AAC GAC CAA CTA CCC CGA TCA TCA GTT ATC CTT AAG GTC TCT
  91  TTT GTG TGG TGC GTT CCG GTA TGG GGG GGG CTG CCG CCA GGT TGG
 136  GGG CCG TGA TTT TGT TTG TCG TCA TAG TGG GCC TCC ATG GGG TCC
 181  GCG GCA AAT ATG CCT TGG CGG ATG CCT CTC TCA AGA TGG CCG ACC
 226  CCA ATC GCT TTC GCG GCA AAG ACC TTC GGT CC TGG ACC CGC TGA
 271  CCG ACC CTC CGG GGG TCC GGC GCG TGT ACC ACA TCC AGG CGG GCC
 316  TAC CGG ACC CGT TCC AGC CCC CCA GCC TCC CGA TCA CGG TTT ACT
 361  ACG CCG TGT TGG AGC GCG CCT GCC GCA GCG TGC TCC TAA ACG CAC
 406  CGT CGG AGG CCC CCC AGA TTG TCC GCG GGG CCT CCG AAG ACG TCC
 451  GGA AAC AAC CCT ACA ACC TGA CCA TCG CTT GGT TTC GGA TGG GAG
 496  GCA ACT GTG CTA TCC CCA TCA CGG TCA TGG AGT ACA CCG AAT GCT
 541  CCT ACA ACA AGT CTC TGG GGG CCT GTC CCA TCC GAA CGC AGC CCC
 586  GCT GGA ACT ACT ATG ACA GCT TCA GCG CCG TCA GCG AGG ATA ACC
 631  TGG GGT TCC TGA TGC ACG CCC CCG CGT TTG AGA CCG CCG GCA CGT
 676  ACC TGC GGC TCG TGA AGA TAA ACG ACT GGA CGG AGA TTA CAC AGT
 721  TTA TCC TGG AGC ACC GAG CCA AGG GCT CCT GTA AGT ACG CCC TCC
 766  CGC TGC GCA TCC CCC CGT CAG CCT GCC TCT CCC CCC AGG CCT ACC
 811  AGC AGG GGG TGA CGG TGG ACA GCA TCG GA TGC TGC CCC GCT TCA
 856  TCC CCG AGA ACC AGC GCA CCG TCG CCG TAT ACA GCT TGA AGA TCG
 901  CCG GGT GGC ACG GGC CA AGG CCC CAT ACA CGA GCA CCC TGC TGC
 946  CCC CTG AGC TGT CCG AGA CCC CCA ACG CCA CGC AGC CAG AAC TCG
 991  CCC CGG AAG ACC CCG AGG ATT CGG CCC TCT TGG AGG ACC CCG TGG
1036  GGA CGG TGG CGC CGC AAA TCC CAC CAA ACT GGC ACA TCC CGT CGA
1081  TCC AGG ACG CCG CGA CGC CTT ACC ATC CCC CGG CCA CCC CGA ACA
1126  ACA TGG GCC TGA TCG CCG GCG CGG TGG GCG GCA GTC TCC TGG CAG
1171  CCC TGG TCA TTT GCG GAA TTG TGT ACT GGA TGC ACC GCC GCA CTC
1216  GGA AAG CCC CAA AGC GCA TAC GCC TCC CCA CAT CCG GGA AGA CG
1261  ACC AGC CGT CCT CGC ACC AGC CCT TGT TTT ACT AGA TAC CCC CCC
1306  TTA ATG GGT GCG GGG GGG TCA GGT CTG CGG GGT TGG GAT GGG ACC
1351  TTA ACT CCA TAC AAA GCG AGT CTG GAA GGG GGG AAA GGC GGA CAG
1396  TCG ATA AGT CGG TAG CGG GGG ACG CGC ACC TGT TCC GCC TGT CGC
1441  ACC CAC AGC TTT TTC GCG A
```

FIG.9

```
  1 Met Gly Gly Ala Ala Ala Arg Leu Gly Ala Val Ile Leu Phe Val Val
 17 Ile Val Gly Leu His Gly Val Arg Gly Lys Tyr Ala Leu Ala Asp Ala
 33 Ser Leu Lys Met Ala Asp Pro Asn Arg Phe Arg Gly Lys Asp Leu Pro
 49 Val Leu Asp Pro Leu Thr Asp Pro Pro Gly Val Arg Arg Val Tyr His
 65 Ile Gln Ala Gly Leu Pro Asp Pro Phe Gln Pro Pro Ser Leu Pro Ile
 81 Thr Val Tyr Tyr Ala Val Leu Glu Arg Ala Cys Arg Ser Val Leu Leu
 97 Asn Ala Pro Ser Glu Ala Pro Gln Ile Val Arg Gly Ala Ser Glu Asp
113 Val Arg Lys Gln Pro Tyr Asn Leu Thr Ile Ala Trp Phe Arg Met Gly
129 Gly Asn Cys Ala Ile Pro Ile Thr Val Met Glu Tyr Thr Glu Cys Ser
145 Tyr Asn Lys Ser Leu Gly Ala Cys Pro Ile Arg Thr Gln Pro Arg Trp
161 Asn Tyr Tyr Asp Ser Phe Ser Ala Val Ser Glu Asp Asn Leu Gly Phe
177 Leu Met His Ala Pro Ala Phe Glu Thr Ala Gly Thr Tyr Leu Arg Leu
193 Val Lys Ile Asn Asp Trp Thr Glu Ile Thr Gln Phe Ile Leu Glu His
209 Arg Ala Lys Gly Ser Cys Lys Tyr Ala Leu Pro Leu Arg Ile Pro Pro
225 Ser Ala Cys Leu Ser Pro Gln Ala Tyr Gln Gln Gly Val Thr Val Asp
241 Ser Ile Gly Met Leu Pro Arg Phe Ile Pro Glu Asn Gln Arg Thr Val
257 Ala Val Tyr Ser Leu Lys Ile Ala Gly Trp His Gly Pro Lys Ala Pro
273 Tyr Thr Ser Thr Leu Leu Pro Pro Glu Leu Ser Glu Thr Pro Asn Ala
289 Thr Gln Pro Glu Leu Ala Pro Glu Asp Pro Glu Asp Ser Ala Leu Leu
305 Glu Asp Pro Val Gly Thr Val Ala Pro Gln Ile Pro Pro Asn Trp His
321 Ile Pro Ser Ile Gln Asp Ala Ala Thr Pro Tyr His Pro Pro Ala Thr
337 Pro Asn Asn Met Gly Leu Ile Ala Gly Ala Val Gly Gly Ser Leu Leu
353 Ala Ala Leu Val Ile Cys Gly Ile Val Tyr Trp Met His Arg Arg Thr
369 Arg Lys Ala Pro Lys Arg Ile Arg Leu Pro His Ile Arg Glu Asp Asp
385 Gln Pro Ser Ser His Gln Pro Leu Phe Tyr
```

FIG.10

```
  1  Met Gly Gln Ile Phe Ser Arg Ser Ala Ser Pro Ile Pro Arg Pro Pro
 70  ATG GGC CAA ATC TTT TCC CGT AGC GCT AGC CCT ATT CCG CGA CCG CCC

17  Arg Gly Leu Ala Ala His His Trp Leu Asn Phe Leu Gln Ala Ala Tyr
118  CGG GGG CTG GCC GCT CAT CAC TGG CTT AAC TTC CTC CAG GCG GCA TAT

33  Arg Leu Glu Pro Gly Pro Ser Ser Tyr Asp Phe His Gln Leu Lys Lys
166  CGC CTA GAA CCC GGT CCC TCC AGT TAC GAT TTC CAC CAG TTA AAA AAA

49  Phe Leu Lys Ile Ala Leu Glu Thr Pro Ala Arg Ile Cys Pro Ile Asn
214  TTT CTT AAA ATA GCT TTA GAA ACA CCG GCT CGG ATC TGT CCC ATT AAC

65  Tyr Ser Leu Leu Ala Ser Leu Leu Pro Lys Gly Tyr Pro Gly Arg Val
262  TAC TCC CTC CTA GCC AGC CTA CTC CCA AAA GGA TAC CCC GGC CGG GTG

81  Asn Glu Ile Leu His Ile Leu Ile Gln Thr Gln Ala Gln Ile Pro Ser
310  AAT GAA ATT TTA CAC ATA CTC ATC CAA ACC CAA GCC CAG ATC CCG TCC

97  Arg Pro Ala Pro Pro Pro Pro Ser Ser Pro Thr His Asp Pro Pro Asp
358  CGT CCC GCG CCA CCG CCG CCG TCA TCC CCC ACC CAC GAC CCC CCG GAT

113  Ser Asp Pro Gln Ile Pro Pro Pro Tyr Val Glu Pro Thr Ala Pro Gln
406  TCT GAT CCA CAA ATC CCC CCT CCC TAT GTT GAG CCT ACG GCC CCC CAA

129  Val Leu Pro Val Met His Pro His Gly Ala Pro Pro Asn His Arg Pro
454  GTC CTT CCA GTC ATG CAT CCA CAT GGT GCT CCT CCT AAC CAT CGC CCA

145  Trp Gln Met Lys Asp Leu Gln Ala Ile Lys Gln Glu Val Ser Gln Ala
502  TGG CAA ATG AAA GAC CTA CAG GCC ATT AAG CAA GAA GTC TCC CAA GCA

161  Ala Pro Gly Ser Pro Gln Phe Met Gln Thr Ile Arg Leu Ala Val Gln
550  GCC CCT GGG AGC CCC CAG TTT ATG CAG ACC ATC CGG CTT GCG GTG CAG

177  Gln Phe Asp Pro Thr Ala Lys Asp Leu Gln Asp Leu Leu Gln Tyr Leu
598  CAG TTT GAC CCC ACT GCC AAA GAC CTC CAA GAC CTC CTG CAG TAC CTT

193  Cys Ser Ser Leu Val Ala Ser Leu His His Gln Gln Leu Asp Ser Leu
646  TGC TCC TCC CTC GTG GCT TCC CTC CAT CAC CAG CAG CTA GAT AGC CTT

209  Ile Ser Glu Ala Glu Thr Arg Gly Ile Thr Gly Tyr Asn Pro Leu Ala
694  ATA TCA GAG GCC GAA ACC CGA GGT ATT ACA GGT TAT AAC CCA TTA GCC
```

FIG.18

```
225  Gly Pro Leu Arg Val Gln Ala Asn Asn Pro Gln Gln Gln Gly Leu Arg
742  GGT CCC CTC CGT GTC CAA GCC AAC AAT CCA CAA CAA CAA GGA TTA AGG

241  Arg Glu Tyr Gln Gln Leu Trp Leu Ala Ala Phe Ala Ala Leu Pro Gly
790  CGA GAA TAC CAG CAA CTC TGG CTC GCC GCC TTC GCC GCC CTG CCG GGG

257  Ser Ala Lys Asp Pro Ser Trp Ala Ser Ile Leu Gln Gly Leu Glu Glu
838  AGT GCC AAA GAC CCT TCC TGG GCC TCT ATC CTC CAA GGC CTG GAG GAG

273  Pro Tyr His Ala Phe Val Glu Arg Leu Asn Ile Ala Leu Asp Asn Gly
886  CCT TAC CAC GCC TTC GTA GAA CGC CTC AAC ATA GCT CTT GAC AAT GGG

289  Leu Pro Glu Gly Thr Pro Lys Asp Pro Ile Leu Arg Ser Leu Ala Tyr
934  CTG CCA GAA GGC ACG CCC AAA GAC CCC ATC TTA CGT TCC TTA GCC TAC

305  Ser Asn Ala Asn Lys Glu Cys Gln Lys Leu Leu Gln Ala Arg Gly His
982  TCC AAT GCA AAC AAA GAA TGC CAA AAA TTA CTA CAG GCC CGA GGA CAC

321  Thr Asn Ser Pro Leu Gly Asp Met Leu Arg Ala Cys Gln Thr Trp Thr
1030 ACT AAT AGC CCT CTA GGA GAT ATG TTG CGG GCT TGT CAG ACC TGG ACC

337  Pro Lys Asp Lys Thr Lys Val Leu Val Val Gln Pro Lys Lys Pro Pro
1078 CCC AAA GAC AAA ACC AAA GTG TTA GTT GTC CAG CCT AAA AAA CCC CCC

353  Pro Asn Gln Pro Cys Phe Arg Cys Gly Lys Ala Gly His Trp Ser Arg
1126 CCA AAT CAG CCG TGC TTC CGG TGC GGG AAA GCA GGC CAC TGG AGT CGG

369  Asp Cys Thr Gln Pro Arg Pro Pro Gly Pro Cys Pro Leu Cys Gln
1174 GAC TGC ACT CAG CCT CGT CCC CCC CCC GGG CCA TGC CCC CTA TGT CAA

385  Asp Pro Thr His Trp Lys Arg Asp Cys Pro Arg Leu Lys Pro Thr Ile
1222 GAC CCA ACT CAC TGG AAG CGA GAC TGC CCC CGC CTA AAG CCC ACT ATC

401  Pro Glu Pro Glu Pro Glu Glu Asp Ala Leu Leu Leu Asp Leu Pro Ala
1270 CCA GAA CCA GAG CCA GAG GAA GAT GCC CTC CTA TTA GAC CTC CCC GCT

417  Asp Ile Pro His Pro Lys Asn Ser Ile Gly Gly Glu Val ***
1318 GAC ATT CCA CAC CCA AAA AAC TCC ATA GGG GGG GAG GTT TAA
```

FIG.18(CONT.)

|  | A | B |  |
|---|---|---|---|
| 130,000 |  |  |  |
| 75,000 |  |  |  |
| 55,000 | — |  |  |
| 51,000 | — | — | 50,000 |
| 46,000 | — | — |  |
| 44,000 | — | — | 39,000 |
|  |  |  | 27,000 |
|  |  |  | 17,000 |

FIG. 21

METHOD FOR INCREASING GENE EXPRESSION USING PROTEASE DEFICIENT YEASTS

BACKGROUND OF THE INVENTION

The present invention relates to yeast for enhancing expression of a gene and a method for preparing a protein thereby.

Many studies have recently been conducted for producing useful proteins by yeast, using genetic engineering techniques. The reason is that expression of some genes which had been impossible in a prokaryote such as *Escherichia coli* became possible in yeast, a eukaryote. One example thereof is the expression of hepatitis B virus surface antigen having immunogenicity. When proteins having many disulfide bonds such as human lysozyme are produced, inactive types of human lysozyme are expressed intracellularly or secreted in expression using *Escherichia coli* or *Bacillus subtilis*. However, an active type of human lysozyme is expressed and secreted by yeast [K. Yoshimura et al., Biochem. Biophys. Res. Commun. 145, 712 (1987)].

However, the amounts of foreign genes expressed by yeast are generally lower than those expressed by *Escherichia coli*. Therefore, it is very important for industrial production of foreign proteins to increase the gene expression in yeast.

SUMMARY OF THE INVENTION

The present inventors have discovered that *Saccharomyces cerevisiae* AH22R⁻ strain (IFO 10134, FRI FERM BP-804) provides higher gene expression than other yeasts, and further that this strain is surprisingly respiratory-deficient. As a result of further studies of other yeasts, the present inventors have discovered that respiratory-deficient strains ($\rho^-$) of yeast (recombinant) transformed with expression plasmids of genes provide higher gene expression than their parent strains ($\rho^+$), namely that the gene expression is increased by rendering the yeast respiratory-deficient.

Yeast is able to grow under both anaerobic and aerobic conditions. ATP required for growth of yeast is acquired by a glycolysis system in cytoplasms under anaerobic conditions and by oxidative phosphorylation in mitochondria under aerobic conditions. Therefore, the respiratory-deficient strains ($\rho^-$) can be obtained by deleting a part or whole of mitochondria DNA [Kobo no Kaibo (Anatomy of yeast), edited by Naohiko Yanagishima, Taiji Oshima and Masako Osumi, Kodansha Scientific, p. 137-147, 1981]. The respiratory-deficient strain where whole of the mitochondria DNA is deleted is sometimes represented by $\rho^o$. In this specification, however, $\rho^-$ and $\rho^o$ are totally represented by $\rho^-$.

In accordance with the present invention, there are provided respiratory-deficient yeast except *Saccharomyces cerevisiae* AH22R⁻, said respiratory-deficient yeast being transformed with a DNA containing a gene for foreign protein to yeast, and a method for preparing a foreign protein, which comprises culturing the yeast, accumulating the protein in a culture, and collecting the protein.

BRIEF DESCRIPTION OF THE DRAWINGS

FIG. 2 shows a DNA sequence of the TaqI-XhoI fragment of the human lysozyme gene;

FIG. 3 shows a DNA sequence encoding the modified type of egg white lysozyme signal peptide;

FIG. 8 shows a DNA sequence of the multi-linker used in the present invention.

FIG. 9 shows the base sequence of HSV-1 Miyama strain gD gene, and FIG. 10 shows the amino acid sequence of the gD protein.

FIG. 11 shows the base sequence of a DNA coding for hen egg white lysozyme signal peptide.

FIG. 18 shows the DNA base sequence of the gag gene and the amino acid sequence of the gag protein (*** shows a transcription termination codon).

FIG. 21 shows an SDS-PAGE image of the HTLV-I gag precursor obtained in Example 13 (FIG. 21A and FIG. 21B show an SDS-PAGE image by staining with the silver-staining method and the image by staining with the Western blotting method).

FIG. 23 illustrates a construction method of a 2.0 kbp PstI-SacI fragment coding for the PKCa gene, and FIGS. 24 and 25 illustrate construction schema of pTFE755 and pTFE756, respectively.

DETAILED DESCRIPTION OF THE INVENTION

Figure 1:
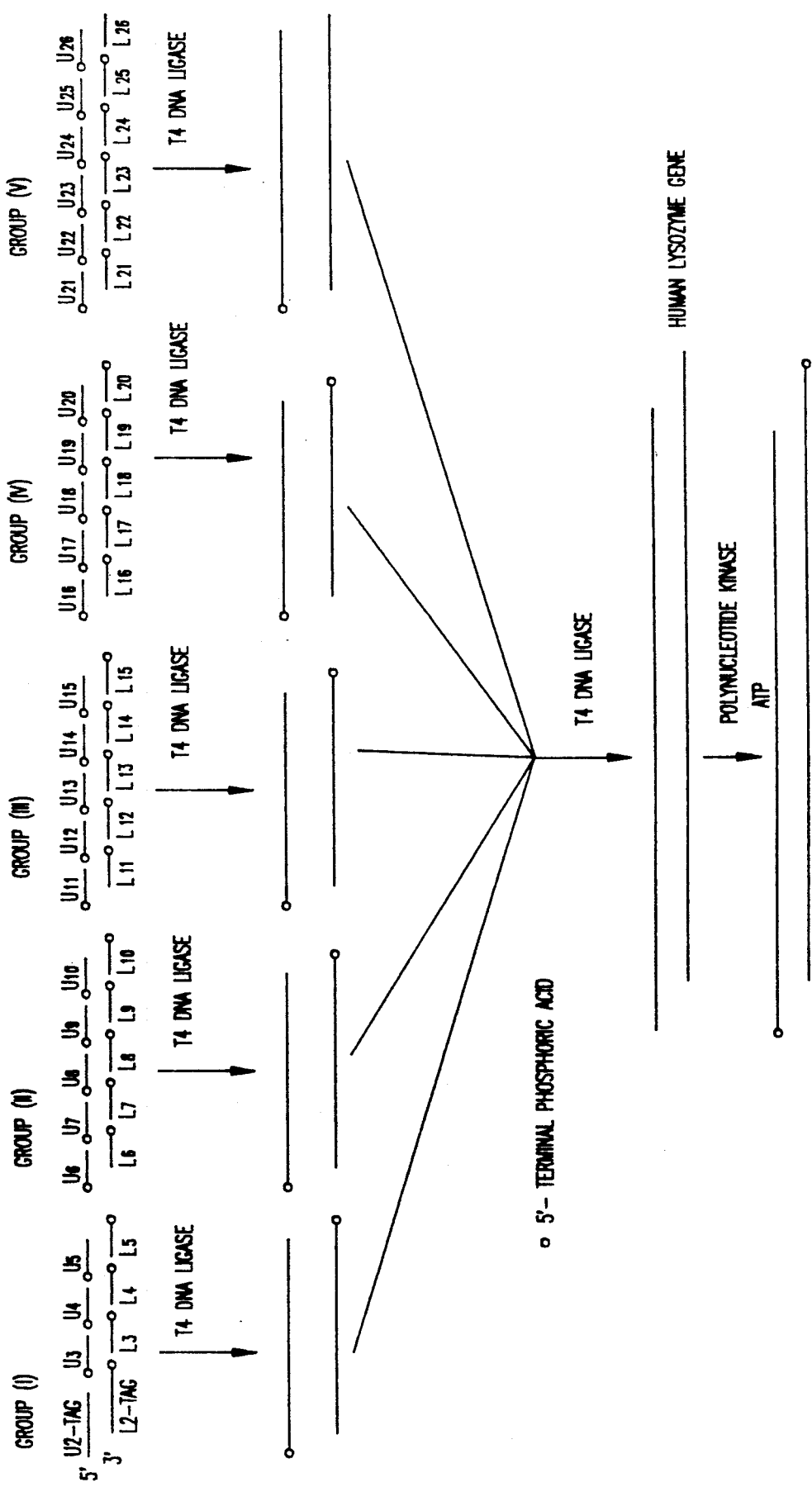
FIG. 1 is a diagram showing a process for synthesizing the synthetic human lysozyme gene by ligation of oligonucleotides.

The yeast strains for use in the present invention include, for example, *Saccharomyces cerevisiae* K33- 7B (a leu2 his pho80 pho8), *Saccharomyces cerevisiae* NA87-11A (α leu2 his3 trp1 pho3 pho5), *Saccharomyces cerevisiae* NA74-3A (a leu2 his4 pho9 can1), *Saccharomyces cerevisiae* NAX-50D (a leu2 his4 ura3 lys1 can1) and the like. *Saccharomyces cerevisiae* K33-7B described above was prepared by crossing *Saccharomyces cerevisiae* NA79-10C [Y. Kaneko et al., Mol. Cell. Biol. 5, 248 (1985)] with *Saccharomyces cerevisiae* AH22R⁻ [A. Miyanohara et al., Proc. Natl. Acad. Sci. U.S.A. 80, 1 (1983)]. *Saccharomyces cerevisiae* NA87-11A is described in Mol. Cell. Biol. 4, 771 (1984). *Saccharomyces cerevisiae* NAX-50D which was obtained by crossing NA74-3A with AX66-1B (α leu2 ura3 lys1 pho3) is a laboratory stock strain of the Institute for Fermentation (IFO), Osaka, Japan, and can be supplied from the Institute.

Any promoter for gene expression can be used as long as it functions in the yeast, which includes, for example, a promoter of glyceraldehyde-3-phosphate dehydrogenase gene (GLD), a promoter of repressive acid phosphatase gene (PHO5), a promoter of uridine-galactose diphosphate-4-epimerase gene (Gal 10), a promoter of galactokinase gene (Gal 1), a promoter of phosphoglycerate kinase gene (PGK), a promoter of alcohol dehydrogenase gene (ADH), a promoter of invertase gene (SUC2), a promoter for histidinol phosphate aminotransferase (HIS5), a promoter of α-factor gene and the like.

The gene product expressed by the yeast in the present invention includes animal enzymes, growth factors, hormones, lymphokines, viral proteins and the like. Examples include human lysozyme, protein disulfide isomerase (PDI), protein kinase C, human EGF (epidermal growth factor), basic FGF, nerve growth factor, growth hormone, insulin, interferon α, interferon β, interferon γ, interleukin 2, hepatitis B virus surface antigen, HTLV-I gag protein, lymphotoxin and the like. Genes of molds or bacteria may also be used.

By ligating a DNA coding for a signal peptide upstream from the gene, the expression may be performed. Any signal peptide can be used as long as it functions in the yeast. Examples include egg white lysozyme and its modified type, human lysozyme, glucoamylase, α-factor, killer factor and the like. The efficiency may be further enhanced by inserting a region coding for a propeptide between a signal peptide-encoding region and a gene to be expressed.

Any vector can be used as long as it functions in the yeast. Examples of the vector include pSH19 [S. Harashima et al., Mol. Cell. Biol. 4, 771 (1984)], pSH19-1 (European Patent Unexamined Publication No. EP-A-0235430) and the like An expression vector can be obtained by inserting a promoter into the vector.

The plasmids for expression of the gene can be obtained by inserting the gene downstream from the promoter in the expression vector described above. In many cases, the gene expression can be increased by inserting a terminator downstream from the gene. The terminator includes those of phosphoglycerate kinase gene (PGK), FLP gene of 2 μDNA, invertase gene (SUC2) and the like.

Methods for constructing the expression plasmid in the present invention are known, one of which is described, for example, in Molecular Cloning (1982), Cold Spring Harbor Laboratory.

Any expression plasmid can be used as long as it expresses the gene in the yeast, producing the gene product either inside cells (intracellular expression) or outside cells (expression and secretion). The expression and secretion plasmid includes expression and secretion plasmids pGEL125 [K. Yoshimura et al., Biochem. Biophys. Res. Commun. 145, 712 (1987)], pGFL735, pGFL725T, pTFL710T, pTFL771T, pTFL780T for human lysozyme, an expression and secretion plasmid pGFE213 for human EGF and the like.

Using the expression plasmid obtained as described above, the yeast is transformed. The transformation methods, which are known per se, include for example the lithium method [Ito et al., J. Bacteriol. 153, 163 (1983)], the protoplast method [Hinnen et al., Proc. Natl. Acad. Sci. U.S.A. 75, 1927 (1978)] and the like. Thus, the yeast (recombinant) having the expression plasmid is obtained.

Methods for obtaining the respiratory-deficient strain (ρ−) from the yeast having respiratory activity (parent strains ρ+), which are known per se, include for example the method described in Laboratory Course Manual for Methods in Yeast Genetics, Cold Spring Harbor Laboratory, 1986. That is, the respiratory-deficient strain can be easily obtained by culturing the parent strain in a medium containing ethidium bromide, and then isolating the strain which can grow in a medium containing glucose as a carbon source, but cannot grow in a medium containing glycerol. Although the frequency is low, the respiratory-deficient strain can also be obtained by single colony isolation from the parent strain. When the parent strain is a transformant (recombinant) having an expression plasmid, the desired recombinant by which gene expression is increased can be directly obtained by isolating its respiratory-deficient strain. When the parent strain carrys no expression plasmid, the desired recombinant can be obtained by isolating its respiratory-deficient strain and then introducing an expression plasmid therein.

The transformant (recombinant) thus obtained is cultured by methods which are known per se.

Examples of the medium include Burkholder minimum medium [K. L. Bostian et al. Amer. J. Bot. 30, 206 (1943)], its modified medium [A. Toh-e et al., J. Bacteriol. 113, 727 (1973)] or lower phosphate medium [A. Toh-e et al., Q. Bacterial 113, 727 (1973)]. The cultivation is generally conducted at 15°to 40° C., preferably 24° to 37° C. for 10 to 168 hours, preferably 72 to 144 hours with or without shaking, aeration or agitation if necessary.

After the completion of the cultivation, the supernatant is separated from the cells by methods which are known per se. For example, to obtain human lysozyme or human EGF remaining within the cells, the cells are disrupted by conventional methods such as a disruption using ultrasonic treatment or French press, mechanical disruption such as crushing and disruption by a cell wall lytic enzyme. Further, if necessary, the human lysozyme thus produced may be extracted by addition of a surfactant such as Triton-X100 or deoxycholate. The human lysozyme or human EGF contained in the supernatant or the extract thus obtained is purified by conventional protein purification methods such as salting out, isoelectric point precipitation, gel filtration, ion-exchange chromatography and high performance liquid chromatography (HPLC, FPLC, etc.) to obtain the desired human lysozyme or human EGF.

The activity of human lysozyme obtained as described above can be assayed by the method described in Yoshimura et al., Biochem. Biophys. Res. Commun. 145, 712 (1987), in which decrease in absorbance of *Micrococcus luteus* cells is used as an index. The human EGF can be determined by the radioimmunoassay supplied by Amersham Inc., the fibroblast receptor assay [Proc. Natl. Acad. Sci. U.S.A. 72, 1371 (1975)], etc.

Gene products other than human lysozyme and human EGF can also be separated and purified by known methods.

The gene expression by the respiratory-deficient yeast is generally increased about 1.5-fold to 10-fold as compared with the parent cell (ρ+).

The present invention will hereinafter be described in detail with the following Reference Examples and Examples. It is understood of course that these Reference Examples and Examples are not intended to limit the scope of the invention.

REFERENCE EXAMPLE 1

Construction of Human Lysozyme Secretory Plasmid pGFL735

After 5 µg of *Escherichia coli* vector pBR322 was reacted with 1.5 units of restriction enzyme BalI in 40 µl of a reaction solution [10 mM Tris-HCl (pH 7.5), 10 mM MgCl₂, 1 mM dithiothreitol] at 37° C. for 5 hours, the reaction mixture was treated with phenol and a DNA fragment was precipitated with ethanol in accordance with conventional methods. To this DNA fragment, 50 ng of a phosphorylated XhoI linker d[pCCTCGAGG] (New England Biolabs) was added and they were ligated with each other by T4 DNA ligase according to a conventional method.

An *Escherichia coli* DH1 strain was transformed with this reaction solution and a plasmid was extracted from the ampicillin-resistant and tetracycline-resistant transformant thus obtained, according to the alkaline extraction method H. C. Birnboim and J. Doly, Nucl. Acids Res., 7, 1513 (1979)] to obtain a plasmid pBR322X having an XhoI site in place of the BalI site.

In the report of Ikehara et al., [Chem. Pharm. Bull. 4, 2202 (1986)], the human lysozyme gene is prepared, for example, from the 52 oligonucleotide blocks shown in Table 1.

This DNA fragment (200 ng) was mixed with 100 ng of the human lysozyme gene fragment prepared above and allowed to ligate with each other in 10 µl of a reaction solution [66 mM Tris-HCl (pH 7.6), 10 mM ATP, 10 mM spermidine, 100 mM MgCl₂, 150 mM DTT, 2 mg/ml BSA, 5 units of T4 DNA ligase] at 14° C. overnight. Using this reaction solution, an *Escherichia coli* DH1 strain was transformed according to the method of Cohen et al. [Proc. Natl. Acad. Sci. U.S.A. 69, 2110 (1972)]. A plasmid was isolated from the transformant thus obtained according to the alkaline extraction method previously mentioned. Their molecular weight and cleavage pattern by restriction enzymes were examined and pLYS221 in which the human lysozyme gene fragment was inserted was obtained. The EcoRI-XhoI fragment of pLYS221 was isolated and its base sequence was determined in accordance with the dideoxynucleotide synthetic chain termination method. As a result, the TaqI-XhoI fragment of human lysozyme gene was obtained as shown in FIG. 2 exactly as assumed.

This sequence codes for the Glu-4 to the Val-130 of the amino acid sequence of human lysozyme.

The Leu-4, the Ile-6 and the Val-8 of the known amino acid sequence of the egg white lysozyme signal peptide [A. Jung et al., Proc. Natl. Acad. Sci. 77, 5759 (1980)] were replaced with Phe, Leu and Ala, respec-

TABLE 1

| Upper Strand No. | Lower Strand No. |
|---|---|
| U1 TCGAGATGAAGGTTT | L26 TCGAGCTATTAAAC |
| U2 TTGAGAGATGCGAAT | L25 ACCACAACCTTGAAC |
| U3 TAGCCAGAACTTTGAAG | L24 GTATTGTCTGACATC |
| U4 AGATTGGGTATGGAC | L23 TCTATTTTGGCATCT |
| U5 GGCTACCGTGGTATT | L22 GTTTCTCCAAGCGAC |
| U6 TCTTTAGCCAACTGG | L21 CCAGGCTCTAATACCCTG |
| U7 ATGTGTCTTGCTAAG | L20 TGGGTCACGGACAAC |
| U8 TGGGAATCCGGCTATAAC | L19 TCTCTTAGCGCAGGC |
| U9 ACTAGAGCTACCAAT | L18 AACAGCATCAGCAAT |
| U10 TACAACGCTGGCGAC | L17 GTTGTCCTGAAGC |
| U11 CGTTCTACAGACTATGG | L16 AAAGCTGAGCAAGAT |
| U12 TATTTTCCAAATTAACT | L15 AAGTGACAGGCGTTGAC |
| U13 CTAGATATTGGTG | L14 GGCACCTGGAGTCTTGC |
| U14 TAACGATGGCAAGACTC | L13 CATCGTTACACCAATAT |
| U15 CAGGTGCCGTCAACGCC | L12 CTAGAGTTAATTTGG |
| U16 TGTCACTTATCTTGC | L11 AAAATACCATAGTCTGT |
| U17 TCAGCTTTGCTTCAG | L10 AGAACGGTCGCCAGC |
| U18 GACAACATTGCTGAT | L9 GTTGTAATTGGTAGC |
| U19 GCTGTTGCCTGCGCT | L8 TCTAGTGTTATAGCCG |
| U20 AAGAGAGTTGTCCGT | L7 GATTCCCACTTAGCAAG |
| U21 GACCCACAGGGTATT | L6 ACACATCCAGTTGGC |
| U22 AGAGCCTGGGTCGCT | L5 TAAAGAAATACCACG |
| U23 TGGAGAAACAGATGC | L4 GTAGCCGTCCATACC |
| U24 CAAAATAGAGATGTC | L3 CAATCTCTTCAAAGT |
| U25 AGACAATACGTTCAAGG | L2 TCTGGCTAATTCGCATC |
| U26 TTGTGGTGTTTAATAGC | L1 TCTCAAAAACCTTCATC |

In Table 1, CGAGAGATGCGAAT was synthesized as U2-taq in place of U2, and TCTGGCTAATTCGCATCTCT was synthesized as L2-taq in place of L2, according to the report of Ikehara et al. Then, using fragments U2-taq, U3 to U26, L2-taq and L3 to L26, the respective hybrids of oligonucleotide blocks were formed according to the report of Ikehara et al. (FIG. 1). After each of these groups was ligated by T4 DNA ligase, both 5'-termini were enzymatically phosphorylated.

2.6 µg of the plasmid pBR322X was reacted with 6 units of restriction enzyme XhoI and 6 units of restriction enzyme ClaI in 35 µl of a reaction solution [33 mM acetate buffer, pH 7.9, 66 mM potassium acetate, 10 mM magnesium acetate, 0.5 mM dithiothreitol, 0.01% BSA] at 37° C. for 1 hour. Then, the solution was deproteinized with phenol and precipitated with cold ethanol.

tively. The nucleotide sequence was determined in consideration of the following points for high expression:

(1) Codons which are frequently used in yeast are preferentially selected;

(2) To enhance the expression, a sequence of the yeast PGK gene is used upstream from ATG; and (3) Construction of a hybrid signal is possible.

The nucleotide sequence thus synthesized is shown in FIG. 3. There are provided an XhoI site at the 5'-terminus and a TaqI site at the 3'-terminus containing the human lysozyme-encoding region. The whole sequence consists of 8 oligonucleotide blocks (#1-#8), which were prepared by the phosphoamidite method [M. H. Caruthers et al., Tetrahedron Letters 22, 1859 (1981)].

The oligonucleotide blocks #2 to #7 were first mixed with each other in 10 µl (5 µg) portions, to which were further added 20 μl of a kinase buffer of a 10-fold concentration (0.5M Tris-HCl, 0.1M MgCl$_2$, 0.1M mercaptoethanol, pH 7.6), 20 μl of 10 mM ATP, 20 μl (50 u) of T4 polynucleotide kinase (Takara Shuzo Inc.) and 80 μl of distilled water. The mixture was then reacted at 37° C. for 2 hours and thereafter treated at 65° C. for 20 minutes to stop the reaction. To this reaction mixture were added the oligonucleotide blocks #1 and #8 in 10 μl (5 μg) portions. Further, 10 μl of T4 ligase (NEB Inc.) was added thereto and the mixture was reacted at 14° C. overnight. The resulting reaction mixture was subjected to 10% polyacrylamide electrophoresis. A 76 bp fragment was cut out and extracted from the gel by electroelution. This fragment was dissolved in 45 μl of distilled water, to which were added 6 μl of the kinase buffer of a 10-fold concentration previously mentioned, 6 μl of 10 mM ATP and 2 μl (5 u) of T4 polynucleotide kinase previously mentioned. The mixture was reacted at 37° C. for 1 hour and then stored at −20° C.

In FIG. 3, there is adopted a single letter expression for amino acids (Rule Confirmed by IUPAC-IUB Biochemistry Nomenclature).
Example:
- A: Alanine
- B: Aspartic acid or asparagine
- C: Cysteine
- D: Aspartic acid
- E: Glutamic acid
- F: Phenylalanine
- G: Glycine
- H: Histidine
- I: Isoleucine
- K: Lysine
- L: Leucine
- M: Methionine
- N: Asparagine
- P: Proline
- O: Glutamine
- R: Arginine
- S: Serine
- T: Threonine
- V: Valine
- Y: Tyrosine
- Z: Glutamic acid or glutamine
- X: Unknown or other amino acids The plasmid pLYS221 (236 μμg) was treated with 120 u of EcoRI (Nippon Gene Inc.) and 120 u of XhoI (Nippon Gene Inc.) at 37° C. for 2 hours to cut out a fragment of the human lysozyme-encoding region. This fragment was further treated with 26 u of TaqI (Nippon Gene Inc.) at 65° C. for 1 hour to cut out a fragment of the human lysozyme-encoding region from which a part of the N-terminal portion was deleted.

About 1 μg of this fragment was mixed with 0.5 μg of a DNA fragment coding for the signal sequence described above and the mixture was reacted in the presence of 800 u of T4 ligase previously mentioned at 16° C. for 16 hours, followed by treatment with XhoI (42 u).

The obtained XhoI fragment (10 ng) was mixed with 1 ng of a fragment obtained by treating yeast expression vector pGLD906-1 (Japanese Patent Unexamined Publication No. 43991/1986) with XhoI, and both were ligated with each other in the presence of T4 ligase.

Figure 4:
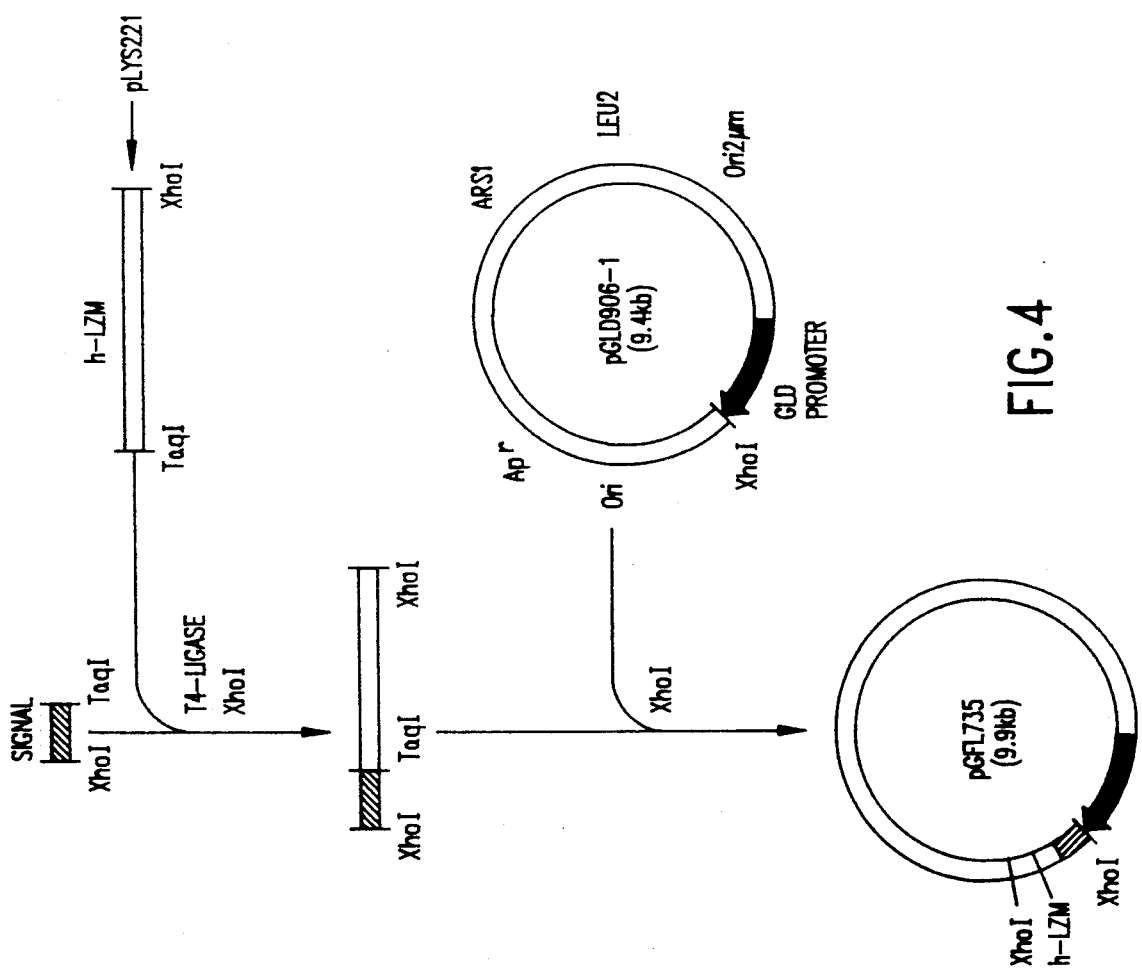
FIGS. 4 to 6 show schemes for the construction of the human lysozyme expression plasmids used in the present invention.

Escherichia coli DH1 was transformed with the resulting reaction mixture by the method described above to obtain a number of plasmids where the signal sequence-encoding region and the human lysozyme gene were inserted downstream from the GLD promoter in the same direction as that of the promoter One of such plasmids was named pGFL735 and used in the following experiments (see FIG. 4).

REFERENCE EXAMPLE 2

Figure 5:
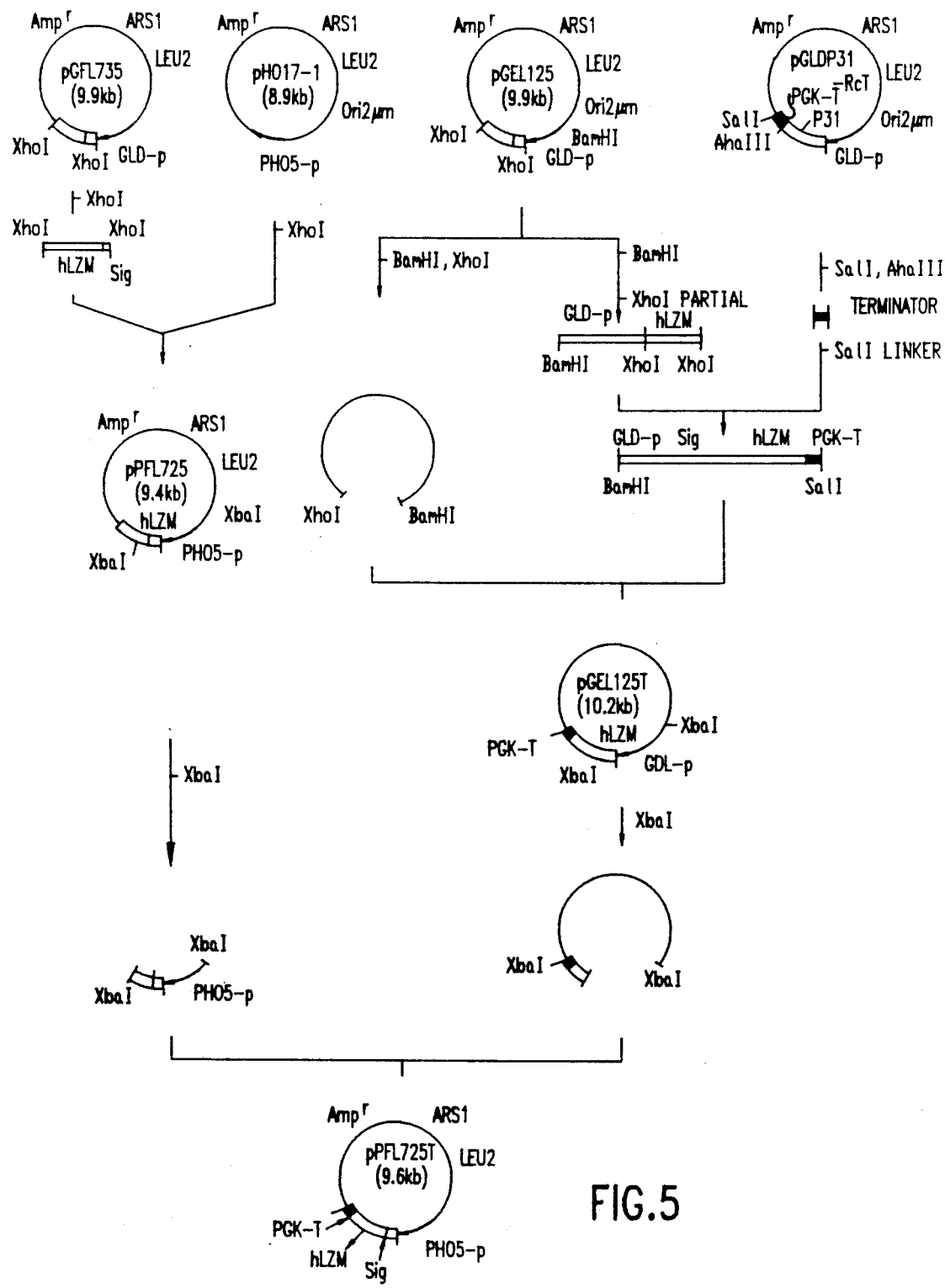

Construction of Human Lysozyme Expression Plasmid pPFL725T (FIG. 5)

A 0.28 kb AhaIII-SalI fragment containing a PGK terminater was isolated from a modified HBsAg P31 expression plasmid pGLD P31-RcT (European Patent Unexamined Publication No. 0235430). An SalI linker pGGTCGACC was ligated with this fragment by T4 DNA ligase, followed by treatment with SalI. The 0.28 kb SalI fragment and the SalI linker not ligated with the fragment were separated by agarose gel electrophoresis and the 0.28 kb SalI fragment was obtained from agarose gel by the isolating method of DNA using DEAE cellulose paper [G. Winberg and M. L. Hammarskjold, Nucl. Acids Res. 8, 253 (1980)].

A human lysozyme expression plasmid pGEL125 using the egg white lysozyme signal peptide [K. Yoshimura et al., Biochem. Biophys. Res. Commun. 145, 712 (1987)] was cleaved with BamHI and XhoI, from which a 1.5 kb BamHI-XhoI fragment containing the GLD promoter and the egg white lysozyme signal peptide-encoding region and the human lysozyme-encoding region, and the residual 8.4 kb BamHI-XhoI fragment were separated by agarose gal electrophoresis. Then, each of them was isolated.

The 0.28 kb SalI fragment containing the PGK terminator was ligated by T4 DNA ligase to the 3'-terminus (XhoI site) of the above-described 1.5 kb BamHI-XhoI fragment containing the GLP promoter, the egg white lysozyme signal peptide-encoding region and the human lysozyme- encoding region, and then subjected to agarose gel electrophoresis to isolate a 1.8 kb BamHI-SalI fragment.

The 1.8 kb BamHI-SalI fragment thus obtained was ligated with the 8.4 kb BamHI-XhoI fragment by T4 DNA ligase. Using the resulting fragment, Escherichia coli DH1 was transformed. A plasmid was prepared from the ampicillin-resistant transformant, and was named pGEL125T.

From the human lysozyme expression plasmid pGFL735 obtained in Reference Example 1, a 0.5 kb XhoI fragment coding for the modified signal peptide and human lysozyme was isolated. On the other hand, an expression vector pPHO17-1 having the PHO-5 promoter (European Patent Unexamined Publication No. 0235430) was cleaved with XhoI and then ligated with the 0.5 kb XhoI fragment, followed by transformation of Escherichia coli. A plasmid was prepared from the ampicillin-resistant transformant thus obtained, and was named pPFL725.

Each of plasmids pGEL125T and pPFL725 obtained as described above had XbaI cleavage sites upstream from the promoter and in the human lysozyme-encoding region. Both plasmids were cleaved with XbaI, and the 1.7 kb XbaI fragment from pPFL725 was ligated with the 7.9 kb XbaI fragment from pGEL125T by T4 DNA ligase, followed by transformation of Escherichia coli DH1. A plasmid was isolated from the ampicillin-resistant transformant thus obtained, and was named pPFL725T.

REFERENCE EXAMPLE 3

Figure 6:
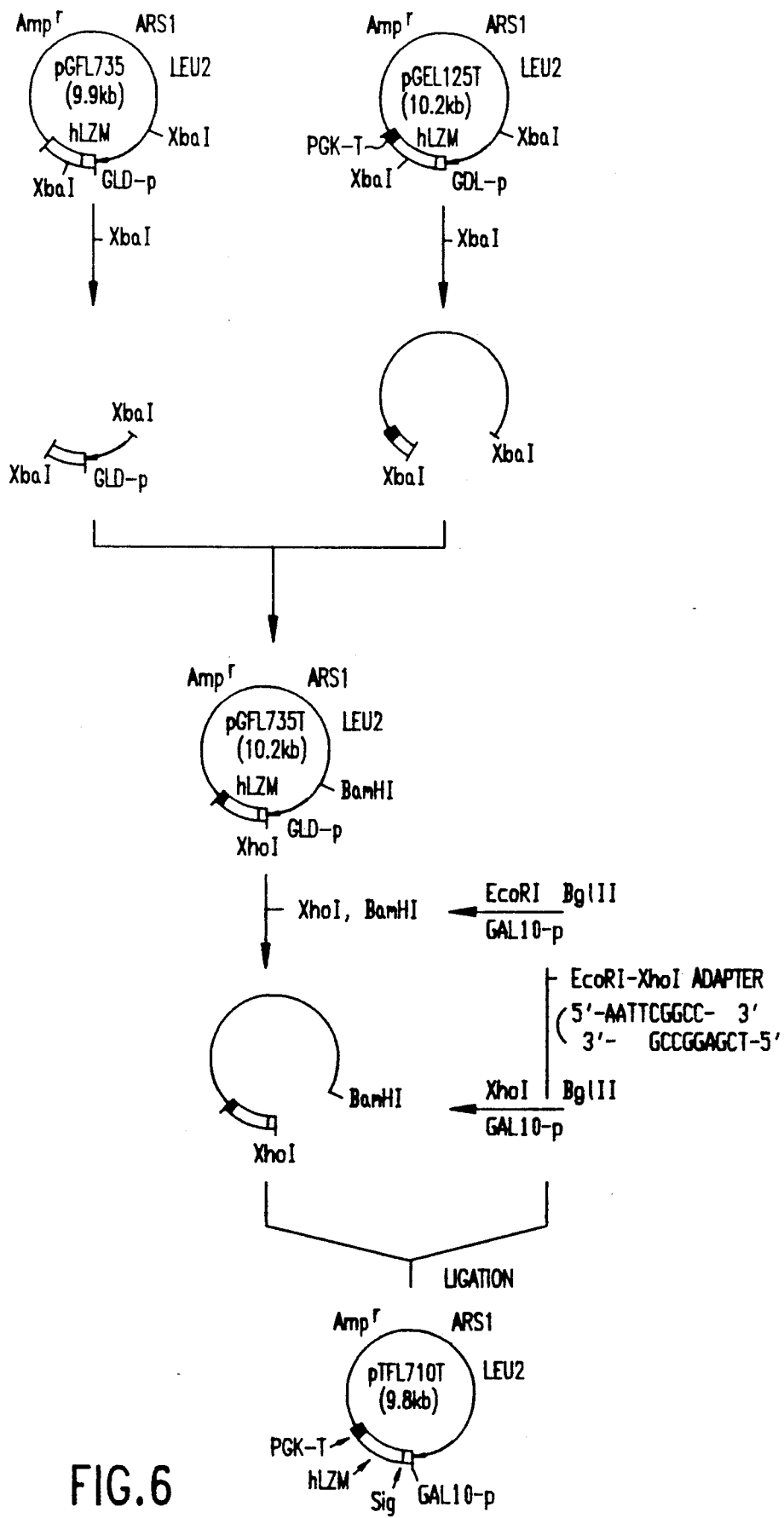

Construction of Human Lysozyme Expression Plasmid pTFL710T (FIG. 6)

A 2.3 kb XbaI fragment and a 7.9 kb XbaI fragment were isolated from the human lysozyme expression plasmid pGFL 735 obtained in Reference Example 1 and from the plasmid pGFL125T obtained in Reference Example 2, respectively. Both fragments were then ligated with each other by T4 DNA ligase, followed by transformation of *Escherichia coli* DH1. A plasmid was isolated from the ampicillin-resistant transformant, and was named pGFL735T.

An EcoRI-XhoI adapter was ligated by T4 DNA ligase with a 0.7 kb BglII-EcoRI fragment containing the Gal 10 promoter obtained from plasmid p286, which was obtained by replacing a 275 bp SalI-BamHI fragment located upstream from the Gal 10 promoter of a plasmid pBM150 [Mol. Cell. Biol. 4, 1440 (1984)] with a multi-linker of about 40 bp having restriction enzyme sites such as SacII, BamHI, SalI and BglII (FIG. 8). The resulting product was then treated with BglII and XhoI, and a 0.7 kb BglII-XhoI fragment was isolated by agarose gel electrophoresis.

On the other hand, the 1.1 kb BamHI-XhoI fragment containing the GLD promoter of the plasmid pGFL735T was removed, and the BglII-XhoI fragment containing the Gal 10 promoter was insereted therein, followed by transformation of *Escherichia coli* DH1. A plasmid was isolated from the ampicillin-resistant transformant thus obtained, and was named pTFL710T.

REFERENCE EXAMPLE 4

Figure 7:
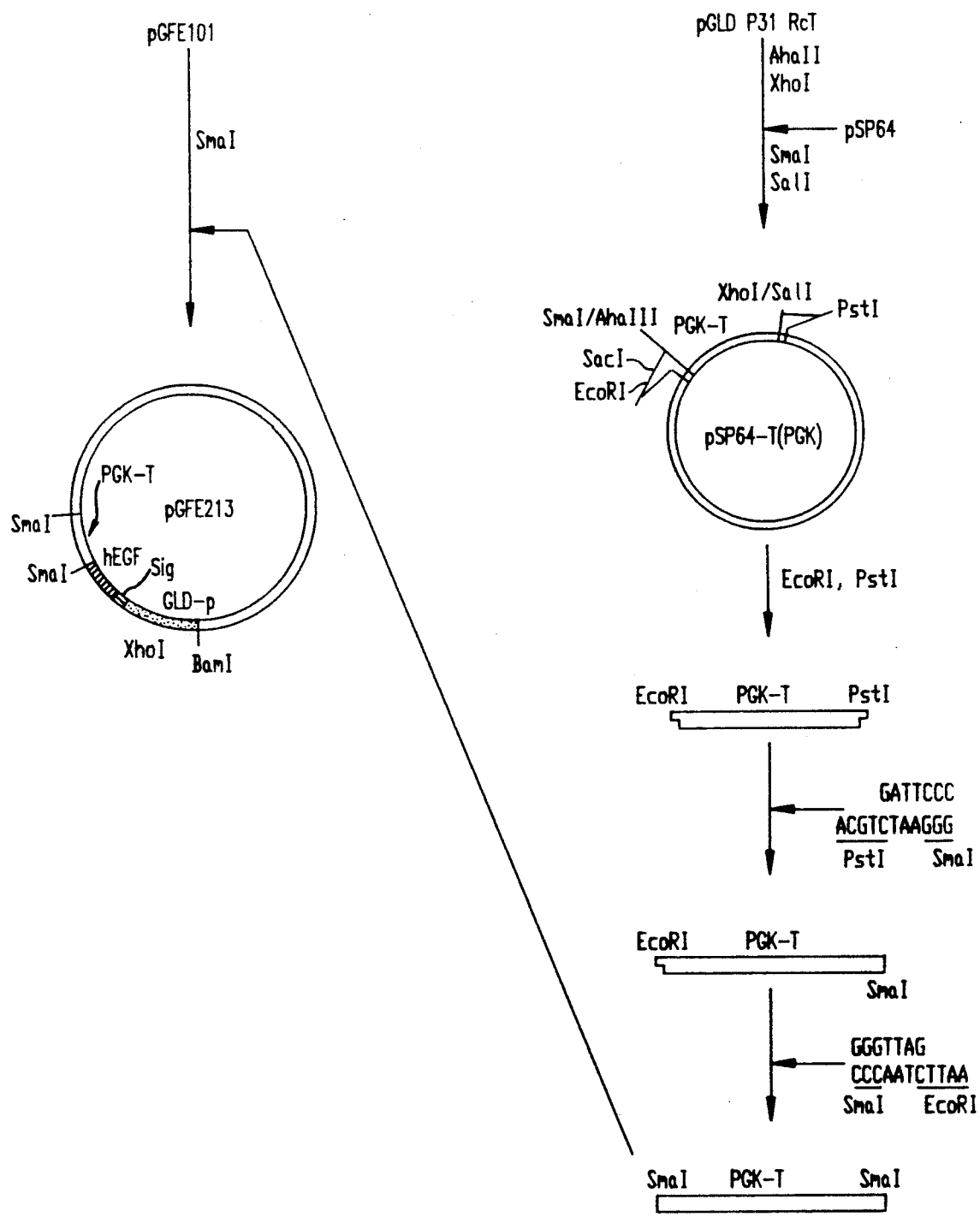
FIG. 7 shows a scheme for the construction of the human EGF expression plasmid used in the present invention.

Construction of Human EGF Expression Plasmid pGFE213 (FIG. 7)

The oligonucleotide block #9 and the oligonucleotide block #10 shown in FIG. 7 were chemically synthesized in place of the oligonucleotide blocks #5 and #7 and the oligonucleotide blocks #6 and #8 shown in FIG. 3 of Reference Example 1, respectively, and ligated with the oligonucleotide blocks #1 to #4 by T4 DNA ligase to prepare a 76 bp XhoI-HinfI fragment coding for a modified type of signal peptide and the N-terminal region of human EGF. A 0.16 kb HinfI-PstI fragment coding for human EGF from which a portion of the N-terminus was removed was isolated from a plasmid pTB370 [Taniyama et al., J. Takeda Res. Lab. 45, 136 (1986), Japanese Patent Unexamined Publication 88881/1986], and to the 5'-terminus thereof was ligated the 76 bp XhoI-HinfI fragment described above by T4 DNA ligase, followed by treatment with XhoI and PstI to isolate a 0.24 kb XhoI-PstI fragment. A PstI-SmaI adapter was ligated with this fragment by T4 DNA ligase, followed by treatment with XhoI and SmaI to isolate a 0.24 kb XhoI-SmaI fragment coding for the modified type signal peptide and human EGF.

Plasmid pGFL735Sm obtained by modifying the XhoI site located downstream from the human lysozyme-encoding region of the plasmid pGFL735 obtained in Reference Example 1 to an SmaI site was cleaved with XhoI and SmaI, and a DNA fragment coding for the modified type of signal peptide and human lysozyme was removed. In place of the removed DNA fragment, the 0.24 kb XhoI-SmaI fragment described above was inserted to obtain plasmid pGFE101.

A 0.28 kb AhaIII-XhoI fragment containing the PGK terminator was isolated from the plasmid pGLD P31-RcT previously mentioned and inserted in the SmaI-SalI site of a plasmid pSP64 (Riboprobe Inc. U.S.A.) to obtain a plasmid pSP64-T (PGK). An EcoRI-PstI fragment containing the PGK terminator was isolated from this plasmid, and the PstI-SmaI adapter and a SmaI-EcoRI adapter were added thereto, followed by insertion of the resulting product into the SmaI site of the plasmid pGFE101 described above to obtain a human EGF expression plasmid pGFE213.

EXAMPLE 1

Preparation of Transformants

Using the human lysozyme expression plasmid pGFL735 obtained in Reference Example 1, *Saccharomyces cerevisiae* K33-7B (a leu2 his pho80 pho8), *Saccharomyces cerevisiae* NA87-11A (α leu2 his3 trp1 pho3 pho5) and *Saccharomyces cerevisiae* NA74-3A (a leu2 his4 pho9 can1) were transformed by the lithium method previously mentioned to obtain transformants *Saccharomyces cerevisiae* K33-7B/pGFL735, *Saccharomyces cerevisiae* NA87-11A/pGFL735 and *Saccharomyces cerevisiae* NA74-3A/pGFL735, respectively.

Using the human lysozyme expression plasmid pPFL725 obtained in Reference Example 2, the human lysozyme expression plasmid pTFL710T obtained in Reference Example 3 and the human FEG expression plasmid pGFE213 obtained in Reference Example 4, *Saccharomyces cerevisiae* NA74-3A was transformed by the lithium method to obtain transformants *Saccharomyces cerevisiae* NA74-3A/pPFL725T, *Saccharomyces cerevisiae* NA74-3A/pTFL710T and *Saccharomyces cerevisiae* NA74-3A/pGFE213, respectively.

Further, using the human lysozyme expression plasmid pTFL710T obtained in Reference Example 3, a transformant of *Saccharomyces cerevisiae* NAX-50D, *Saccharomyces cerevisiae* NAX-50D/pTFL710T, was prepared by the lithium method.

EXAMPLE 2

Preparation of Respiratory-Deficient Strains of Transformants (Recombinants)

Using ethidium bromide in accordance with the method described in "Laboratory Course Manual for Methods in Yeast Genetics (Cold Spring Harbor Laboratory, 1986)", respiratory- deficient strains *Saccharomyces cerevisiae* K33-7B($p^-$)/pGFL735, *Saccharomyces cerevisiae* NA87-11A ($p^-$)/pGFL735, *Saccharomyces cerevisiae* NA74-3A ($p^-$) pGFL735, *Saccharomyces cerevisiae* NA74-3A ($p^-$)/pPFL725T, *Saccharomyces cerevisiae* NA74-3A ($p^-$)/pTFL710T, *Saccharomyces cerevisiae* NAX-50D ($p^-$) /pTFL710T and *Saccharomyces cerevisiae* NA74-3A ($p^-$)/pGFE213 were prepared from the transformants (recombinants), *Saccharomyces cerevisiae* K33-7B/pGFL735, *Saccharomyces cerevisiae* NA87-11A/pGFL735, *Saccharomyces cerevisiae* NA74-3A/pGFL735, *Saccharomyces cerevisiae* NA74-3A/pPFL725T, *Saccharomyces cerevisiae* NA74-3A/pTFL710T, *Saccharomyces cerevisiae* NAX50D/pTFL710T and *Saccharomyces cerevisiae* NA74-3A/pGFE213, respectively, which were obtained in Example 1.

EXAMPLE 3

Preparation of Transformant (Recombinant) of Respiratory-Deficient Strain

From *Saccharomyces cerevisiae* NA74-3A, its respiratory-deficient strain ($p^-$) was separated by the method shown in Example 2, and transformed according to the lithium method with the human lysozyme expression plasmid pTFL710T prepared in Reference Example 3 to obtain a transformant *Saccharomyces cerevisiae* NA74-3A ($p^-$)/pTFL710T.

EXAMPLE 4

Secretory Production of Human Lysozyme Using Plasmid pGFL 735

The recombinants obtained in Example 1, *Saccharomyces cerevisiae* K33-7B/pGFL735, *Saccharomyces cerevisiae* NA87-11A/pGFL735 and *Saccharomyces cerevisiae* NA74-3A/pGFL735, and their respiratory-deficient strains obtained in Example 2, *Saccharomyces cerevisiae* K33-7B ($p^-$)/pGFL735, *Saccharomyces cerevisiae* NA87-11A ($p^-$)/pGFL735 and *Saccharomyces cerevisiae* NA74-3A ($p^-$)/pGFL735 were inoculated into modified Burkholder medium containing 8.9% sucrose, 1.1% glucose and 0.044% $KH_2PO_4$ [A. Toh-E et al., J. Bacteril. 113, 727 (1973)], and cultured at 30° C. for 3 days with shaking. 1 ml of each of the culture was transferred to a test tube containing 4 ml of the same medium and cultured at 30° C. for 1 day with shaking. Subsequently, 2 ml of the culture was transferred to a 200 ml Erlenmeyer flask containing 18 ml of the same medium and cultured at 30° C. for 72 hours with shaking. The cultures thus obtained were centrifuged and the human lysozyme activity of the supernatants was measured by the method described in Yoshimura et al., Biochem. Biophys. Res. Commun. 145, 712 (1987) to determine the amounts of human lysozyme produced in the supernatants. The results are shown in Table 2.

TABLE 2

| Recombinant | Cultivation time (hour) | Growth (Klett) | Human lysozyme (mg/L) |
| --- | --- | --- | --- |
| S. cerevisiae K33-7B/pGFL735 | 72 | 443 | 0.5 |
| S. cerevisiae K33-7B($p^-$)/pGFL735 | 72 | 432 | 3.3 |
| S. cerevisiae NA87-11A/pGFL735 | 72 | 470 | 2.5 |
| S. cerevisiae NA87-11A($p^-$)/pGFL735 | 72 | 440 | 5.3 |
| S. cerevisiae NA74-3A/pGFL735 | 72 | 520 | 1.4 |
| S. cerevisiae NA74-3A($p^-$)/pGFL735 | 72 | 490 | 6.0 |
| S. cerevisiae NA74-3A/pPFL725T | 120 | 540 | 3.3 |
| S. cerevisiae NA74-3A($p^-$)/pPFL725T | 120 | 500 | 6.7 |
| S. cerevisiae NA74-3A/pTFL710T | 144 | 530 | 2.0 |
| S. cerevisiae NA74-3A/($p^-$)/pTLF710T | 144 | 505 | 18 |
| S. cerevisiae NAX-50D/pTFL710T | 96 | 405 | 0.9 |
| S. cerevisiae NAX-50D($p^-$)/pTFL710T | 96 | 380 | 5.3 |

As apparent from Table 2, when the human lysozyme expression plasmid pGFL735 having the GLD promoter was used, the human lysozyme production by the respiratory-deficient strain ($p^-$) was 2 to 6 times higher than that by its parent strain ($p^-$) in all yeast strains.

EXAMPLE 5

Secretory Production of Human Lysozyme Using Plasmid pPFL725T

The recombinant *Saccharomyces cerevisiae* NA74-3A/pPFL725T obtained in Example 1 and its respiratory-deficient strain *Saccharomyces cerevisiae* NA74-3A($p^-$)/pPFL725T obtained in Example 2 were inoculated into high phosphate medium [A. Toh-E et al., J. Bacteriol. 113, 727 (1973)] and cultured at 30° C. for 3 days with shaking. 1 ml of each of the culture was transferred to a test tube containing 4 ml of the same medium and cultured at 30° C. for 1 day with shaking. Subsequently, 2 ml of the culture was transferred to a 200 ml Erlenmeyer flask containing 18 ml of low phosphate medium [the modified Burkholder medium previously mentioned which contained 8.9% sucrose, 1.1% glucose and 0.003% $KH_2PO_4$] and cultured at 30° C. for 120 hours with shaking.

The human lysozyme activity of the supernatants of the cultures thus obtained was measured to determine the amounts of human lysozyme produced in the supernatants.

As a result, it was revealed that the respiratory-deficient strain ($p^-$) showed the human lysozyme production about 2 times higher than its parent strain ($p^+$), also when the human lysozyme expression plasmid pPFL725T having the PHO5 promoter was used (Table 2).

EXAMPLE 6

Secretory Production of Human Lysozyme Using Plasmid pTFL710T

The recombinant *Saccharomyces cerevisiae* NA74-3A/pTFL710T obtained in Example 1 and its respiratory-deficient strain *Saccharomyces cerevisiae* NA74-3A($p^-$)/pTFL710T obtained in Example 2 were inoculated into the modified Burkholder medium previously mentioned which contained 8.9% sucrose, 1.1% glucose and 0.044% $KH_2PO_4$ and cultured at 30° C. for 3 days with shaking. 1 ml of each of the culture was transferred to a test tube containing 4 ml of the same medium and cultured at 30° C. for 1 day with shaking. Subsequently, 2 ml of the culture was transferred to a 200 ml Erlenmeyer flask containing 18 ml of a galactose medium [the modified Burkholder medium previously mentioned which contained 8.9% sucrose, 5% galactose, 0.25% glucose and 0.044% KH2P04] and cultured at 30° C. for 144 hours with shaking.

The human lysozyme activity of the supernatants of the cultures thus obtained was measured to determine the amounts of human lysozyme produced in the supernatants.

As a result, it was revealed that the respiratory-deficient strain ($p^-$) showed the human lysozyme production about 2 times higher than its parent strain ($p^+$), also when the human lysozyme expression plasmid pTFL710T having the Ga110 promoter was used (Table 2).

The recombinant *Saccharomyces cerevisiae* NA74-3A/pTFL710T obtained in Example 1 and the transformant of its respiratory-deficient strain, *Saccharomyces cerevisiae* NA74-3A($p^-$)/pTFL710T, obtained in Example 3 were cultured in a similar manner. Similarly to the results described above, the human lysozyme production by *Saccharomyces cerevisiae* NA74-

3A(p⁻)/pTFL710T was higher than that by *Saccharomyces cerevisiae* NA74-3A/pTFL710T.

The transformant *Saccharomyces cerevisiae* NAX-50D/pTFL710T obtained in Example 1 and its respiratory-deficient strain *Saccharomyces cerevisiae* NAX-50D(p⁻)/pTFL710T were cultured in a similar manner for 96 hours. Consequently, the latter produced human lysozyme in quantity about 6 times higher than the former (Table 2).

EXAMPLE 7

Secretory Production of Human EGF Using Plasmid pGFE213

The recombinant *Saccharomyces cerevisiae* NA74-3A/pGFE213 obtained in Example 1 and its respiratory-deficient strain *Saccharomyces cerevisiae* NA74-3A(p⁻)/pGFE213 obtained in Example 2 were cultured in the same manner as in Example 4. The cultures thus obtained were centrifuged and human EGF in the supernatants was determined by use of a kit for radioimmunoassay (Amersham Inc.). The results are shown in Table 3.

TABLE 3

| Recombinant | Growth (Klett) | Human EGF (mg/L) |
|---|---|---|
| *S. cerevisiae* NA74-3A/pGFE213 | 525 | 0.56 |
| *S. cerevisiae* NA74-3A(p⁻)/pGFE213 | 475 | 0.85 |

As described above, the human EGF production by the respiratory deficient strain (p⁻) was higher than that by its parent strain (p⁻), also when the human EGF gene was used as a gene.

REFERENCE EXAMPLE 5

Construction of Human Lysozyme Expression Plasmid pTFL771T

The EcoRI-XhoI adapter was ligated by T4 DNA ligase with the 0.7 kb BglII-EcoRI fragment containing the Gal 10 promoter, which was shown in Reference Example 3. The resulting product was then treated with Sau3AI and XhoI, and subjected to agarose gel electrophoresis to isolate a 0.51 kb Sau3AI-XhoI fragment containing the Gal10 promoter.

On the other hand, the 1.1 kb BamHI-XhoI fragment containing the GLD promoter was removed from the plasmid pGFL735T, which was obtained in Reference Example 3, and the above-described 0.51 kb Sau3AI-XhoI fragment containing the Gal 10 promoter was ligated by T4 DNA ligase in place of the removed fragment. A plasmid was isolated from the transformant of *Escherichia coli* DH1, and was named pTFL771T.

REFERENCE EXAMPLE 6

Construction of Human Lysozyme Expression Plasmid pTFL780T

The 0.7 kb BamHI-XhoI fragment containing the Gal10 promoter was removed from the plasmid pTFL710 obtained in Reference Example 3, and the 0.51 kb Sau3AI-XhoI fragment obtained in Reference Example 5 was inserted in place of the removed fragment to obtain human lysozyme expression plasmid pTFL780T.

EXAMPLE 8

Preparation of Transformants

Using the human lysozyme expression plasmid pTFL771T obtained in Reference Example 5 and the human lysozyme expression plasmid pTFL780T obtained in Reference Example 6, *Saccharomyces cerevisiae* NA74-3A and its respiratory-deficient deficient strain *Saccharomyces cerevisiae* NA74-3A (p⁻) (Example 3) were transformed according to the lithium method to obtain transformants *Saccharomyces cerevisiae* NA74-3A/pTFL771T, *Saccharomyces cerevisiae* NA74-3A (p⁻)/pTFL771T, *Saccharomyces cerevisiae* NA74-3A/pTFL780T and *Saccharomyces cerevisiae* NA74-3A (p⁻)/pTFL780T, respectively.

EXAMPLE 9

Secretory Production of Human Lysozyme Using Plasmids pTFL771T and pTFL780T

The transformants obtained in Example 8 were cultured in a similar manner as in Example 6 and the amount of human lysozyme produced by each transformant was determined. As a result, in each case of pTFL771 and pTFL780T, the transformant of the respiratory-deficient strain produced more human lysozyme than did the transformant of its parent strain, as in Example 6.

EXAMPLE 10

Secretion of Human Lysozyme Using α-Factor Promoter and Pre-pro Region

The DNA fragment containing the GLD promoter and signal peptide-coding region in the plasmid pGEL125 was substituted with a DNA fragment containing the promoter and pre-pro region of α-factor gene which was derived from p69A[Cell, 30, 933(1982)] to construct a plasmid pAAL410 for secretion of human lysozyme.

On the other hand, *Saccharomyces cerevisiae* NA74-3A was crossed with *Saccharomyces cerevisiae* DK-13D (α leu2 his3 trp1)[Mol. Cell. Biol., 4, 771 (1984)] to prepare *Saccharomyces cerevisiae* TA39 (α leu2 his can1), from which respiratory-deficient strain *Saccharomyces cerevisiae* TA39 (p⁻) was obtained according to the method described in Example 2.

The above *Saccharomyces cerevisiae* TA39 and its respiratory-deficient strain *Saccharomyces cerevisiae* TA39 (p⁻) were transformed with the above plasmid pAAL410 for secretion of human lysozyme by the lithium method to give *Saccharomyces cerevisiae* TA39-/pAAL410 and *Saccharomyces cerevisiae* TA39(p⁻)-/pAAL410, respectively.

The transformants *Saccharomyces cerevisiae* TA39-/pAAL410 and *Saccharomyces cerevisiae* TA39(p⁻)-/pAAL410 were cultivated in the same method as that of Example 4 and the obtained supernatant of the culture was subjected to an assay for human lysozyme activity to determine the yield of human lysozyme. The assay showed that *Saccharomyces cerevisiae* TA39-/pAAL410 and *Saccharomyces cerevisiae* TA39(p⁻)-/pAAL410 produced 0.5 mg/l and 2.6 mg/l of human lysozyme, respectively. That is, the respiratory-deficient strain (latter) yielded human lysozyme five times as much as the parent strain (former).

REFERENCE EXAMPLE 7

Preparation of Virus DNA of Herpes Simplex Virus Miyama Strain

Vero cells [African Green Monkey (*Cercopithecus aethiops*) kidney cells] were infected with 0.05–0.5 PFU/cell of herpes simplex virus type 1 (ESV-1) Miyama strain and cultivated at 37° C. When the cells were denatured sufficiently, the culture where the infected cells were suspended was recovered and centrifuged in a low revolution (3,000 rpm, 10 minutes) for separation into a supernatant and cells. The cells were disrupted by freeze-thawing (freeze-thawing was repeated three times at −80° C. and 37° C.), and a tenfold volume of the supernatant was added to the cells. The mixture was subjected to centrifugation in a low revolution (3,000 rpm, 10 minutes) to remove the cell residue, and the obtained supernatant was added to the previously obtained supernatant. The resulting supernatant was centrifuged at 25,000 rpm for 4 hours to remove a supernatant, and a pellet containing virus particles was obtained. A phosphate-buffered physiological saline [0.8% NaCl, 0.02% KCl, 0.115% $Na_2HPO_4$, 0.02% $KH_2PO_4$ (pH 7.2)] was added to the pellet to prepare a virus suspension. To the suspension 10 μg/ml of DNase I and 0.3 mg/ml of RNase A were added, and the mixture was reacted at 37° C. for 1 hour. Further, 1/5 volume of 5×STEP (0.5% SDS, 50 mM Tris-HCl, pH 7.5, 0.4M EDTA, 0.1% Proteinase K) was added, and the reaction was carried out at 50° C. for 1 hour. The resulting mixture was treated with an equal volume of phenol-chloroform (1:1) and chloroform successively, to give an aqueous layer containing DNA. The aqueous layer was dialyzed against TE buffer [10 mM Tris-HCl (pH 8.0), 1 mM EDTA] overnight. Cold ethanol was added to the inner solution, and the mixture was centrifuged (12,000 rpm, 20 minutes) to remove a supernatant. The obtained precipitate (DNA) was airdried and then dissolved in TE solution (10 mM Tris-HCl, pH 8.0, 1 mM EDTA).

REFERENCE EXAMPLE 8

Construction of Plasmid Containing HSV-1 Miyama Strain DNA Fragment

About 2 μg of the obtained HSV-1 DNA was treated with 30 units of restriction enzyme BamHI (Takara Shuzo) in 30 μl of a reaction medium [10 mM Tris-HCl (pH 8.0), 7 mM $MgCl_2$, 100 mM NaCl, 2 mM 2-mercaptoethanol] at 37° C. for 1 hour, deprotenized with phenol and precipitated with cold ethanol.

About 100 ng of pBR322 which was previously digested with restriction enzyme BamHI in the same manner as above was mixed with about 200 ng of the above-mentioned BamHI-digested HSV-1 DNA, and the reaction was carried out in a reaction mixture [66 mM Tris-HCl (pH 7.6), 66 mM $MgCl_2$, 10 mM dithiothreitol, 1 mM ATP, 300 units of T4 DNA ligase (Takara Shuzo)] at 16° C. overnight to ligate the DNAs. *Escherichia coli* DH-1 was transformed with the resulting reaction mixture, and a plasmid DNA was isolated from an ampicilin-resistant transformant (HSV-1 DNA library) by the alkaline extraction method [T. Maniatis et al., "Molecular Cloning", Cold Spring Harbor Laboratory, P366 (1982)]. The plasmid DNA was digested with restriction enzyme BamHI and then subjected to electrophoresis on 0.8% agarose (Sigma) slab gel in a buffer [0.04M Tris-acetate, 0.002M EDTA (pH 8.0)] at 100V for about 1 hour.

A plasmid DNA containing the DNA fragment of about 5.5 kb to 7.5 kb was again subjected to gel electrophoresis, and DNA fragments on agarose gel were transferred onto nitrocellulose filters (S & S, BA85) [Southern blotting method, T. Maniatis et al., "Molecular Cloning", Cold Spring Harbor Laboratory, P382 (1982)].

On the other hand, based upon the base sequence for HSV-1 Patton strain gD protein as reported in R. J. Watson et al. [Science, 218, 381 (1982)], there were synthesized a base chain (5'-GGCGGCAGTCCCCC-CCAT-3') which was complementary with the base sequence corresponding to the N-terminal of the gD protein, and a base chain (5'-CTAG-TAAAACAAGGGCTG-3') which was complementary with the base sequence corresponding to the C terminal. These two kinds of oligonucleotides were treated with T4 polynucleotide kinase (Takara Shuzo) in 50 μl of a reaction mixture [0.1 μg of oligonucleotide, 50 mM Tris-HCl, pH 8.0, 10 mM $MgCl_2$, 10 mM 2-mercaptoethanol, 50 μCi $\gamma$-$^{32}$pATP (75,000 Ci/mmol), 3 units of T4 polynucleotide kinase] at 37° C. for 1 hour to label the 5' end of the oligonucleotides with $^{32}$P.

The two kinds of oligonucleotide probes labeled by the above method were separately hybridized with the DNA-fixed filters. The hybridization reaction was carried out in 3 ml of a mixture containing 6×SSC [150 mM NaCl, 15 mM sodium citrate (pH 7.0)] containing 10 μCi probe, 5×Denhardt solution, 0.5% SDS, 10 mM EDTA and 100 μg/ml denatured salmon sperm DNA at 37° C. for 16 hours, and then the filter was washed with 5×SSC and 0.1% SDS twice at room temperature and twice at 40° C. for 30 minutes [T. Maniatis et al., "Molecular Cloning", Cold Spring Harbor Laboratory, P309 (1982)].

The autoradiography of the washed filters showed that a DNA fragment having about 6.6 kb was reacted with the two kinds of probes. The DNA fragment of about 6.6 kg was double digested with restriction enzymes DraI (Takara Skhuzo) and NruI (Takara Shuzo) to prepare a DNA fragment of about 1.5 kg. The base sequence of the DNA fragment was determined by the dideoxynucleotide chain termination method [J. Messing et al., Nucleic Acids Research, 9, 309 (1981)] (FIG. 9).

The results showed that all of the amino acid sequence of HSV-1 Miyama strain gD protein was encoded in the 1.5 kb DNA fragment. The amino acid sequence deduced from the base sequence is shown in FIG. 10. The base sequence resembled that of the Patton strain gD protein, but was substituted by 3 bases (different in 2 amino acid residues). Further, it was different from the Hzt strain [Donald J. Dowbenko et al., DNA, 3, 23 (1984)] by addition of 3 bases and substitution with 7 bases (difference in 9 amino acid residues). These results proved that the 1.5 kb DNA fragment encoded HSV-1 Miyama strain gD protein.

The pBR322 into which the above 6.6 kb DNA was inserted was named pHSD BJ-1.

REFERENCE EXAMPLE 9

Construction of Expression Plasmid for HSV-1 Miyama Strain gD Gene-1

(1) Preparation of 72 bp DNA Fragment Encoding Signal Sequence

Based upon the known amino acid sequence of hen egg white lysozyme signal peptide [Jung, A. et al., Proc. Natl. Acad. Sci. USA, 77, 5759 (1980)], there was used a synthetic oligonucleotide having an XhoI site at the 5' end and an SacII site at the 3' end as shown in FIG. 11. The whole sequence which consisted of 8 oligonucleotide blocks (#1, #2, #3, #4, #5, #6, #7, #8) was synthesized by the phosphamidite method [Caruthers, M. H. et al., Tetrahedron Letters, 22, 1859 (1981)].

First, 10 μl (5 μg) each of #2 to #7 was mixed, to which then 20 μl of a tenfold concentrated kinase buffer [0.5M Tris-HCl, 0.1M MgCl$_2$, 0.1M mercaptoethanol, pH 7.6], 20 μl of 10 mM ATP, 2 μl (50U) of T4 polynucleotide kinase (Takara Shuzo) and 80 μl of distilled water were added. The reaction was carried out at 37° C. for 2 hours and then terminated by treatment at 65° C. for 20 minutes. To the mixture 10 μl (5 μg) each of #1 and #8 was added, and the reaction was carried out with 1 μl of T4 ligase (NEB) at 14° C. overnight. The reaction mixture was subjected to 6% polyacrylamide gel electrophoresis, and a 72 bp fragment was cut out, extracted from the gel by electroelution and dissolved in 20 μl of distilled water.

(2) Construction of Expression Plasmid

A plasmid vector pUC18 was cleaved with restriction enzymes HindIII and HincII, and about 200 ng of the resulting vector DNA was reacted with about 1.4 kg HindIII-NruI fragment containing the gD-coding region by T4 DNA ligase (Takara Shuzo) to construct a plasmid pUC19gD.

About 2 μg of the obtained pUC18gD was reacted with 30 units of restriction enzyme SacI (Takara Skhuzo) in 500 μl of a reaction medium [10 mM Tris-HCl (pH 8.0), 7 mM MgCl$_2$, 7 mM 2-mercaptoethanol] at 37° C. overnight, and then partially digested with restriction enzyme SacII to construct an SacII-SacI fragment of about 1.27 kb.

Figure 12:
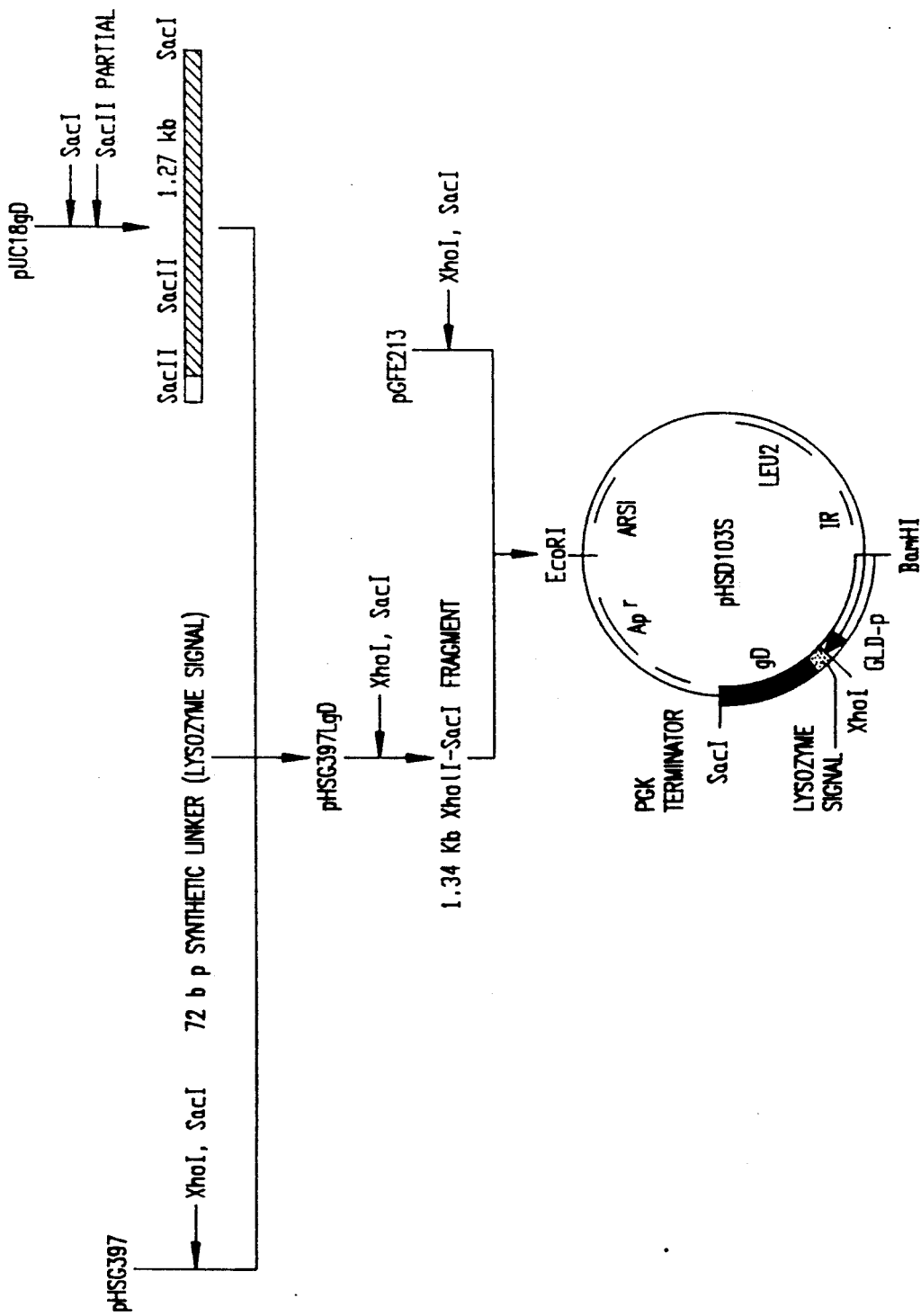
FIGS. 12, 13, 14 and 15 illustrate construction schema of pHSD103S, pHSD105S, pHSD104S and pHSD100, respectively.

The 72 bp synthetic linker (FIG. 11) synthesized in the above (1) and the SacII-SacI fragment of about 1.27 kb were reacted with an XhoI-SacI-digested product of a plasmid vector pHSG397 (Takara Shuzo) to construct a subcloning plasmid pHSG397LgD. The plasmid was digested with restriction enzymes XhoI and SacI, and the obtained XhoI-SacI DNA fragment of about 1.34 kb was reacted with an XhoI-SacI-Digested product of the plasmid pGFE213 described in Reference Example 4 to give an expression plasmid pHSD103S (FIG. 12).

REFERENCE EXAMPLE 10

Construction of Expression Plasmid for HSV-1 Miyama Strain gD Gene-2

Figure 13:
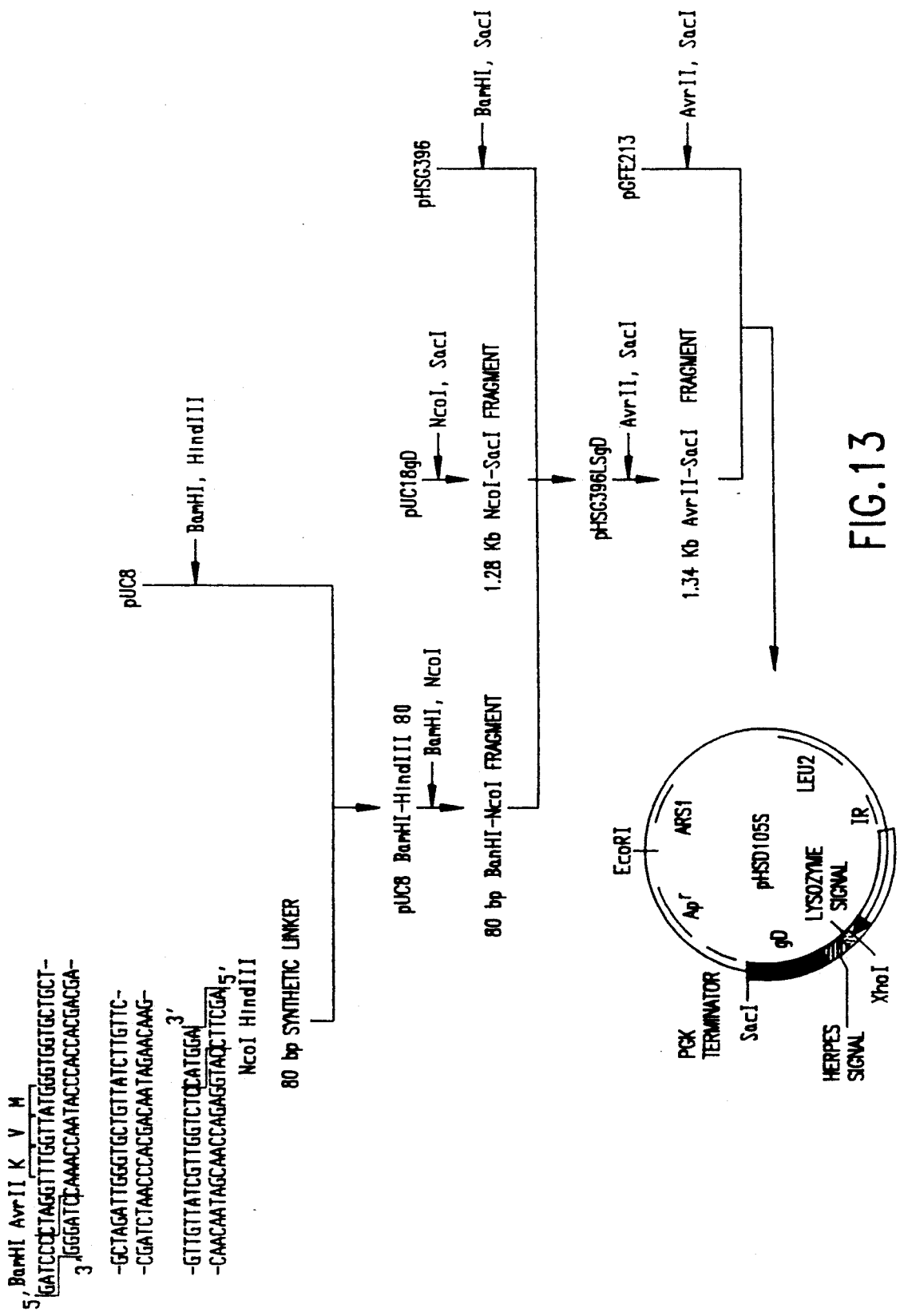

A DNA coding for the N-terminal 2 amino acid residues of human lysozyme and subsequently the N-terminal 20 amino acid residues of the gD, i.e. a DNA fragment of 80 bp shown in FIG. 13, was chemically synthesized and inserted into pUC8 which was previously digested with BamHI and HindIII.

The obtained plasmid pUC8BamHI-HindIII was digested with BamHI and NcoI, and the obtained 80 bp fragment and a NcoI-SacI DNA fragment obtained by digestion of pUC18gD with NcoI and SacI were reacted with an BamHI-SacI-digested product of a plasmid vector pHSG396 (Takara Shuzo) to construct a subcloning plasmid pHSG396LSgD. The plasmid was digested with restriction enzymes AvrII and SacI, and the obtained AvrII-SacI DNA fragment of about 1.34 kb was reacted with an AvrII-SacI-digested product of the plasmid pGFE213 described in Reference Example 4 to construct an expression plasmid pHSD105S (FIG. 13).

REFERENCE EXAMPLE 11

Construction of Expression Plasmid for HSV-1 Miyama Strain gD Gene-3

Figure 14:
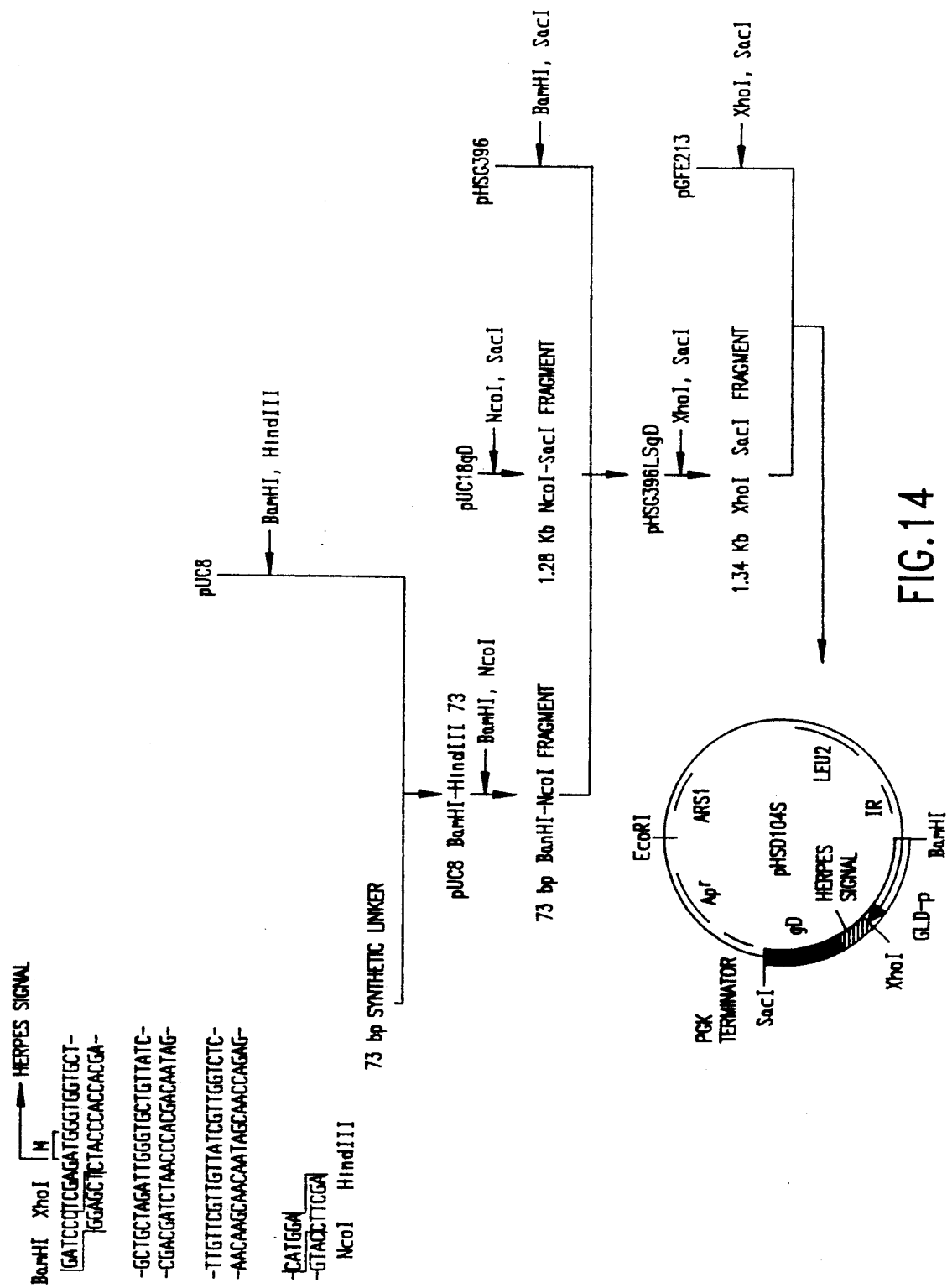

A DNA coding for the N-terminal 20 amino acid residues of the gd, i.e. a 73 bp DNA fragment shown in FIG. 14, was chemically synthesized and inserted into a vector pUC8 which was previously digested with BamHI and HindIII.

The obtained pUC8BamHI-HindIII73 was digested with BamHI and NcoI, and the obtained 73 bp fragment and the above NcoI-SacI DNA fragment of about 1.28 kb were reacted with a BamHI-SacI-Digested product of a plasmid vector pHSG396 to construct a subcloning plasmid pHSG396SgD. The plasmid was digested with restriction enzymes XhoI and SacI, and the obtained 1.34 kb XhoI-SacI DNA fragment was reacted with an XhoI-SacI-digested product of the plasmid pGFE213 described in Reference Example 4 to construct an expression plasmid pHSD104S (FIG. 14).

REFERENCE EXAMPLE 12

Construction of Expression Plasmid for HSV-1 Miyama Strain gD Gene-4

The HindIII-NruI fragment of about 1.4 kb containing the gD-coding region was reacted with about 200 ng of an HindIII-HincII-digested vector pHSG397 by T4 DNA ligase (Takara Shuzo) to construct a plasmid pHSG397gD.

About 2 μg of the obtained pHSG397gD was reacted with 30 units of restriction enzyme HindIII (Takara Shuzo) in 500 μl of a reaction medium [10 mM Tris-HCl (pH 8.0), 7 mM MgCl$_2$, 50 mM NaCl, 7 mM 2-mercaptoethanol] at 37° C. overnight, reacted with DNA polymerase I (Klenow fragment), and then digested with 30 units of restriction enzyme XbaI at 37° C. overnight. The obtained fragment of about 1.4 kb containing the gD-coding region was reacted with about 200 ng of an HincII-XbaI-cleaved vector pHSG396 by T4 DNA ligase (Takara Shuzo) to construct a plasmid pHSG396gD.

Figure 15:
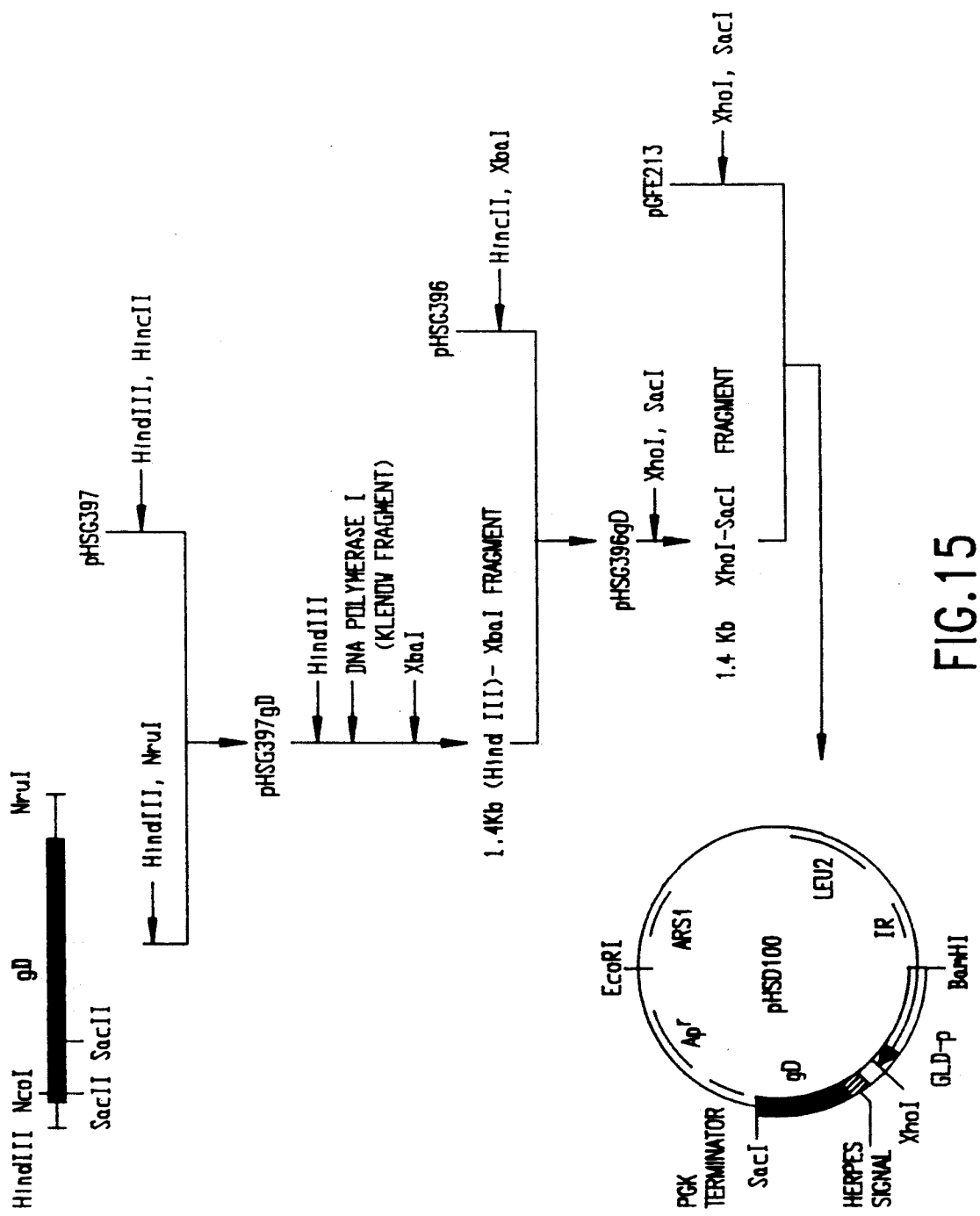

About 2 μg of the obtained pHSG396gD was reacted with 30 units of restriction enzymes SacI and XhoI, and the prepared DNA fragment of about 1.4 kb containing the gD-coding region was reacted with an XhoI-SacI-digested product of the plasmid pGFE213 described in Reference Example 4 to give an expression plasmid pHSD100 (FIG. 15).

EXAMPLE 11

Expression of HSV-1 Miyama Strain gD Gene in Yeast

Yeasts *Saccharomyces cerevisiae* AH22R$^-$ and NA74-3A($p^-$) were transformed with the plasmid pHSD103S constructed in Reference Example 9, the plasmid pHSD104S constructed in Reference Example 11, the plasmid pHSD105S constructed in Reference Example 10 and the plasmid pHSD100 constructed in Reference Example 12, to give transformants AH22R⁻/pHSD103S, AH22R⁻/pHSD104S, AH22R⁻/pHSD105S, AH22R⁻/pHSD100, NA74-3A($p^-$)/pHSD103S, NA74-3A($p^-$)/pHSD104S, NA74-3A($p^-$)/pHSD105S and NA74-3A($p^-$)/pHSD100.

Each of the obtained yeast transformants NA74-3A($p^-$)/pHSD103S, NA74-3A($p^-$)/pHSD104S and NA74-3A($p^-$)/pHSD105A was cultivated in the medium described in Example 15 of European Patent Publication EP-A-0235430, and the cells were collected and washed with 0.9% NaCl. About 200 mg of the cells were suspended in 500 μl of a sodium phosphate buffer [100 mM sodium phosphate (pH 8.1), 7.4M urea, 1% Triton X-100, 0.1 mM (p-amidinophenyl) methanesulfonyl fluoride hydrochloride], and agitated vigorously with 1 g of glass beads by Vortex for about 20 minutes. The mixture was subjected to centrifugation at 10,000 rpm for 5 minutes to obtain a supernatant. An equal volume of twofold concentrated Laemmli buffer was added to the extract. The mixture was heated at 100° C. for 10 minutes, and then cooled and subjected to centrifugation at 10,000 rpm for 5 minutes to obtain a supernatant. The obtained extract (40 μl) was subjected to SDS-polyacrylamide gel electrophoresis, and then electrically blotted on a nitrocellulose filter. The filter was reacted with anti-herpes virus type 1 (Maclntype) rabbit antibody (Dakopatts), and then with horseradish peroxidase-labeled anti-rabbit antibody. The coloring with a development reagent (Bio Rad) showed plural specific bands at the position of 50 to 60 kilodaltons.

REFERENCE EXAMPLE 13

Construction of Expression Vector pGLD907T

Figure 16:
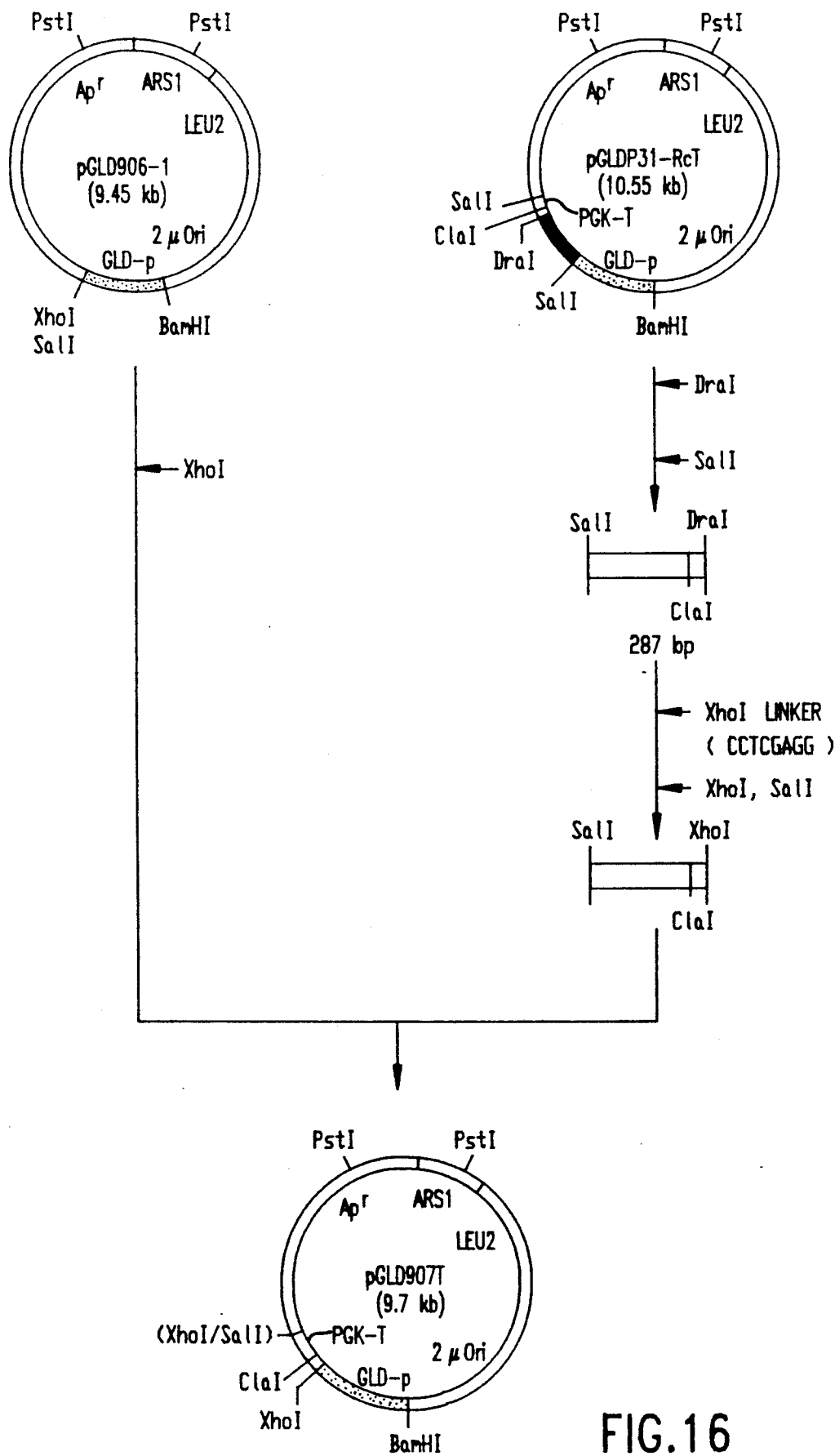
FIG. 16 illustrates a construction scheme of a plasmid pGLD 907T to be used in Reference Example 16.

The expression vector pGLD907T was constructed by inserting into the XhoI site of an expression vector pGLD906-1 [Itoh., Y. et al., Biochem. Biophys. Res. Commun., 138, 268(1986)] a DNA fragment which was obtained by addition of an XhoI linker d(CCTCGAGG) to a 287 bp DraI-SalI DNA fragment obtained from a plasmid pGLD P31-RcT (European Patent Publication EP-A-0235430) (FIG. 16).

REFERENCE EXAMPLE 14

Preparation of gag Gene

Figure 17:
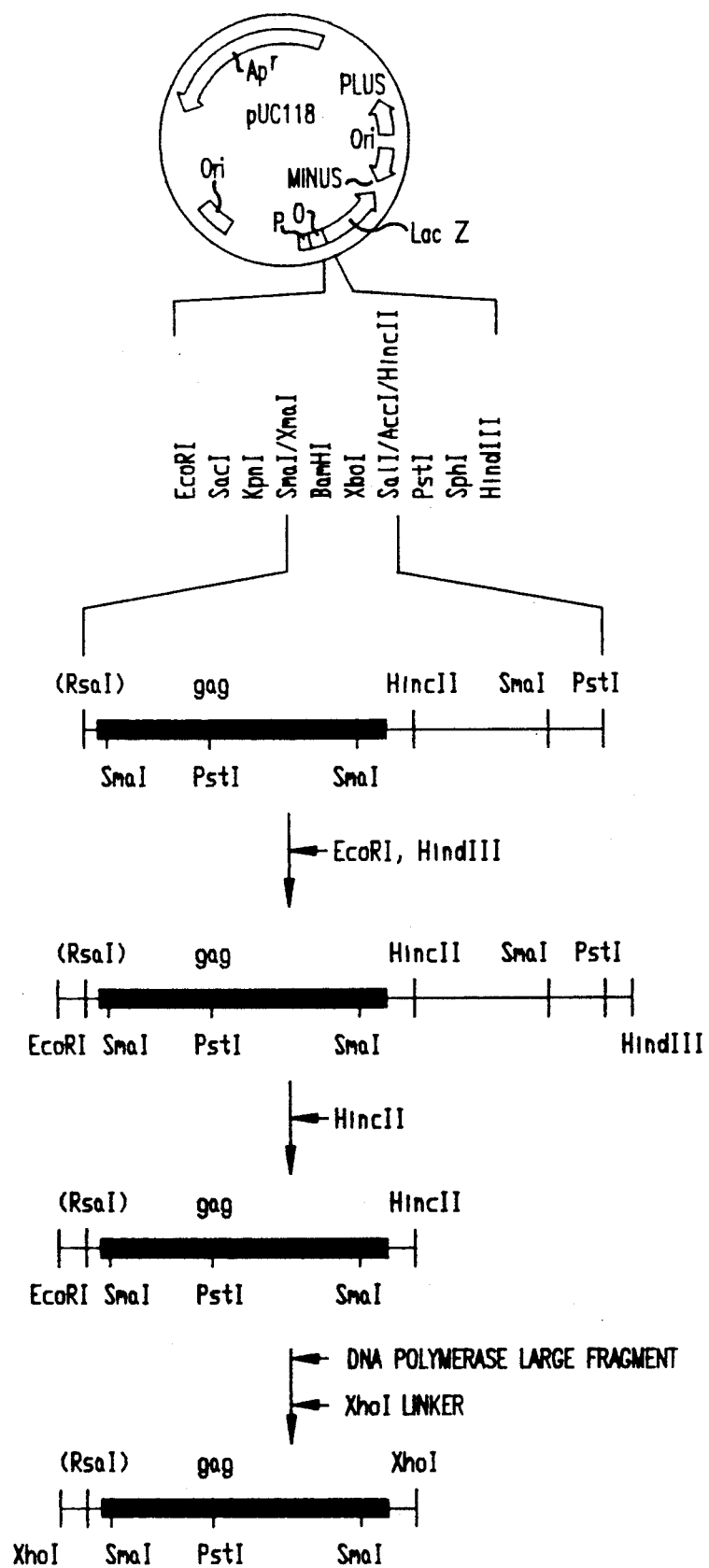
FIG. 17 shows a preparation method of the gag gene described in Reference Example 14.

A known HTLV-I provirus HTLV IC [S. H. Nam et al., Biochem. Biophys. Res. Commun., 139, 129(1986)] was partially digested with RsaI and PstI to prepare a 2.3 kb DNA fragment containing the region of 3'-end LTR(part)-gag-prt-pol(part). The fragment was inserted into pUC118 (Takara Shuzo) digested with SmaI and PstI. The recombinant DNA was digested with EcoRI and HindIII to prepare a 2.3 kb DNA fragment containing the gag gene, and then the fragment was digested with HincII to prepare a 1.5 kb DNA fragment containing 3'-end LTR(part)-gag-prt(part). The fragment was treated with DNA polymerase I large fragment (Takara Shuzo), and an XhoI linker was added to the fragment with T4 DNA ligase and then the fragment was digested with XhoI to expose XhoI sites (FIG. 17). The DNA base sequence of the gag gene contained in the fragment is shown in FIG. 18.

REFERENCE EXAMPLE 15

Construction of Expression Plasmid-1

Figure 19:
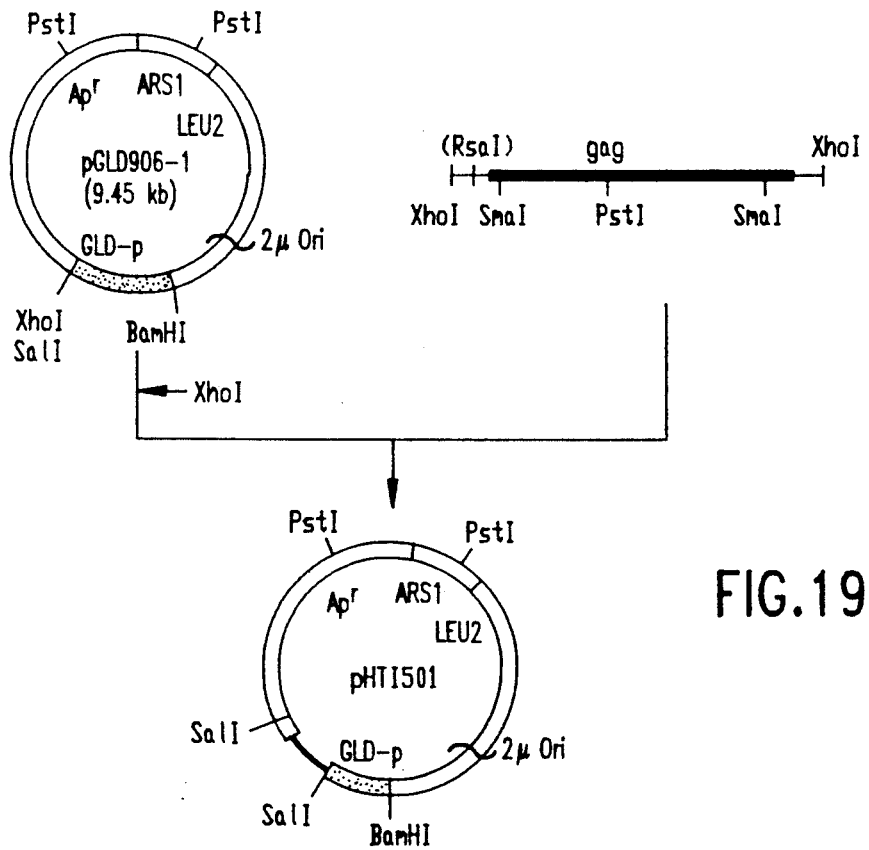
FIGS. 19 and 20 illustrate construction schema of expression plasmids pHTI 501 obtained in Reference Example 15 and pHTI 511 obtained in Reference Example 16.

The gag gene having XhoI sites at both ends which was obtained in Reference Example 14 was inserted into a yeast expression plasmid pGLD906-1 [Y. Itoh et al., Biochem. Biophys. Res. Commun., 138, 268 (1986)] which was previously digested with XhoI to construct an expression plasmid pHTI 501 (FIG. 19).

REFERENCE EXAMPLE 16

Construction of Expression Plasmid-2

Figure 20:
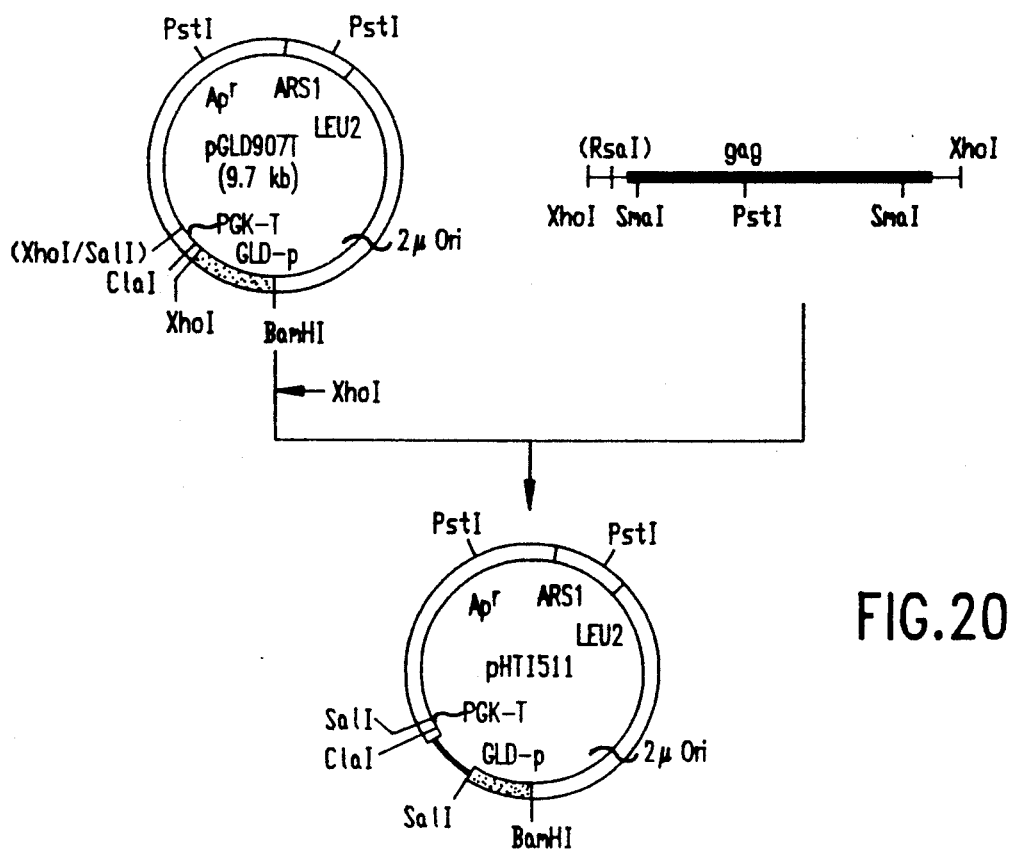

The gag gene having XhoI sites at both ends which was obtained in Reference Example 14 was inserted into a yeast expression plasmid pGLD907T (described in Reference Example 13) which was previously digested with XhoI to construct an expression plasmid pHTI 511 (FIG. 20).

EXAMPLE 12

Preparation and Cultivation of Yeast Transformants and Expression of gag Protein Yeast Saccharomyces cerevisiae NA74-3A($p^-$) was transformed with plasmids pHTI 501 and pHTI 511 obtained in Reference Examples 15 and 16 by the protoplast method [A. Hinnen et al., Proc. Natl. Acad. Sci. USA, 75, 1927 (1978)] to obtain transformants Saccharomyces cerevisiae NA74-3A ($p^-$)/pHTI 501 and Saccharomyces cerevisiae NA74-3A($p^-$)/pHTI 511, respectively.

Each of these yeast transformants was cultivated at 30° C. for 3 days with shaking in 5 ml of a culture medium [3 g of $K_2HPO_4$, 50 g of glucose, 4 g of L-asparagine, 100 mg of L-histidine, 0.1 mg of KI, 500 mg of $MgSO_4 \cdot 7H_2O$, 330 mg of $CaCl_2 \cdot 2H_2O$, 0.4 mg of $CuSO_4 \cdot 5H_2O$, 2.5 mg of $FeSO_4 \cdot 7H_2O$, 0.4 mg of $MnSO_4 \cdot 4H_2O$, 0.2 mg of $(NH_4)_3PO_4 \cdot 12MoO_3 \cdot 3H_2O$, 3.1 mg of $ZnSO_4 \cdot 7H_2O$, 10 mg of inositol, 0.2 mg of thiamine, 0.2 mg of pyridoxine, 0.2 mg of Ca-pantothenate, 0.2 mg of niacin and 0.002 mg of biotin, per 1], and 0.5 ml of the culture was transferred to 4.5 ml of another culture broth having the same composition as mentioned above and cultivated at 30° C. for 1 day. Then, 2 ml of the culture was transferred to 18 ml of a fresh medium [400 mg of $KH_2PO_4$, 80 g of sucrose, 5 g of L-asparagine, 300 mg of L-histidine, 2.0 g of KCl, 0.1 mg of KI, 650 mg of $MgSO_4 \cdot 7H_2O$, 429 mg of $CaCl_2 \cdot 2H_2O$, 10 g of glucose, 25 mM of Tris-maleic acid (pH 6.5), 0.4 mg of $CuSO_4 \cdot 5H_2O$, 2.5 mg of $FeSO_4 \cdot 7H_2O$, 0.4 mg of $MnSO_4 \cdot 4H_2O$, 0.2 mg of $(NH_4)_3PO_4 \cdot 12MoO_3 \cdot 3H_2O$, 3.1 mg of $ZnSO_4 \cdot 7H_2O$, 10 mg of inositol, 0.2 mg of thiamine, 0.2 mg of pyridoxine, 4.0 mg of Ca-pantothenate, 4.0 mg of niacin and 0.040 mg of biotin, per 1] and cultivated at 30° C. with shaking. After 72 hours, the culture was sampled and centrifuged (10,000×g, 10 minutes) for separation into a supernatant and cells.

The cells (20 mg, wet weight) were suspended in 100 μl of an SDS-gel sample buffer [U. K. Laemmli, Nature, 227, 680(1970)] and then heated at 100° C. for 10 minutes to extract proteins. The solubilized proteins were fractionated by 12.5% SDS-polyacrylamide gel electrophoresis, and then transferred onto a nitrocellulose filter according to the known Western blotting method [H. Towbin et al., Proc. Natl. Acad. Sci. USA, 76, 4350(1979)]. The screening of the HTLV-I gag protein by a known anti-p19 murine monoclonal antibody GIN 7 [S. Itamura et al., Gene, 38, 57 (1985)] revealed that a gag precursor of 53 kDal was expressed.

EXAMPLE 13

The transformed yeast cells (50 g wet weight) obtained by cultivating Saccharomyces cerevisiae NA74-3A($p^-$)/pHTI 511 according to the method of Example 14 were suspended in 50 ml of a 50 mM potassium phosphate buffer (pH 7.4) containing 1.2M sorbitol and 14 mM 2-mercaptoethanol, and treated with 200 μg/ml of Zymolyase 100T (Seikagaku Kogyo) at room temperature for 1.5 hours. The resulting mixture was diluted with 250 ml of a 50 mM potassium phosphate buffer (pH 7.4) containing 0.1% Triton X-100, 0.1 mM (paraamidinophenyl)methanesulfonyl fluoride (APMSF) and allowed to stand at room temperature for 1.5 hours to disrupt the cells. The lysate was centrifuged at 14,000 rpm for 20 hours to remove the supernatant, and then 125 ml of a 1/150M phosphate buffer (pH 7.0) containing 8M quanidine hydrochloride was added to the precipitate. The mixture was stirred at room temperature for 2 hours to extract the gag precursor, and then centrifuged at 14,000 rpm for 20 minutes to obtain a supernatant as a crude extract.

The crude extract was diluted fortyfold with a 1/150M phosphate buffer (pH 7.0) containing 0.5M urea, 0.25% Nonidet P40, 15 mM EDTA, 1mM phenylmethanesulfonyl fluoride (PMSF) and 0.1 mM APMSF. An anti-p19 murine monoclonal antibody [Tanaka et al., Gann, 74, 327(1983)]-bound Formyl-Cellulofine (Seikagaku Kogyo) column having a bed volume of 5 ml which was previously equilibrated with the same buffer was charged with the obtained dilution and washed with the above-described buffer for dilution and then a 1/150M phosphate buffer (pH 7.0) containing 1M quanidine hydrochloride. The HTLV-I gag precursor was eluted with a 1/150M phosphate buffer (pH 7.0) containing 3M quanidine hydrochloride from the column.

The eluate from the antibody column was subjected to high performance liquid chromatography equipped with YMC-PACK $C_4$ (Yamamura Kagaku), and eluted by increasing the concentration of acetonitrile from 20% to 100% linearly in the presence of 0.1% trifluoroacetic acid (TFA). The gag precursor was eluted in an acetonitrile concentration of about 65% later than yeast-derived other proteins. The solvents were removed to yield 117 μg of the gag precursor.

The HTLV-I gag precursor thus obtained was subjected to polyacrylamide gel electrophoresis containing sodium dodecyl sulfate (SDS-PAGE) and stained by the silver-staining method to mainly stain a band of 51 KDal as shown in FIG. 21A. Further, bands of 55, 46 and 44 KDal were observed. This silver-stained image was well identical with the image of Western blotting using horseradish peroxidase-conjugated anti-p19 murine monoclonal antibody GIN-7 (FIG. 21B).

REFERENCE EXAMPLE 17

Construction of Expression Vector

Figure 22:
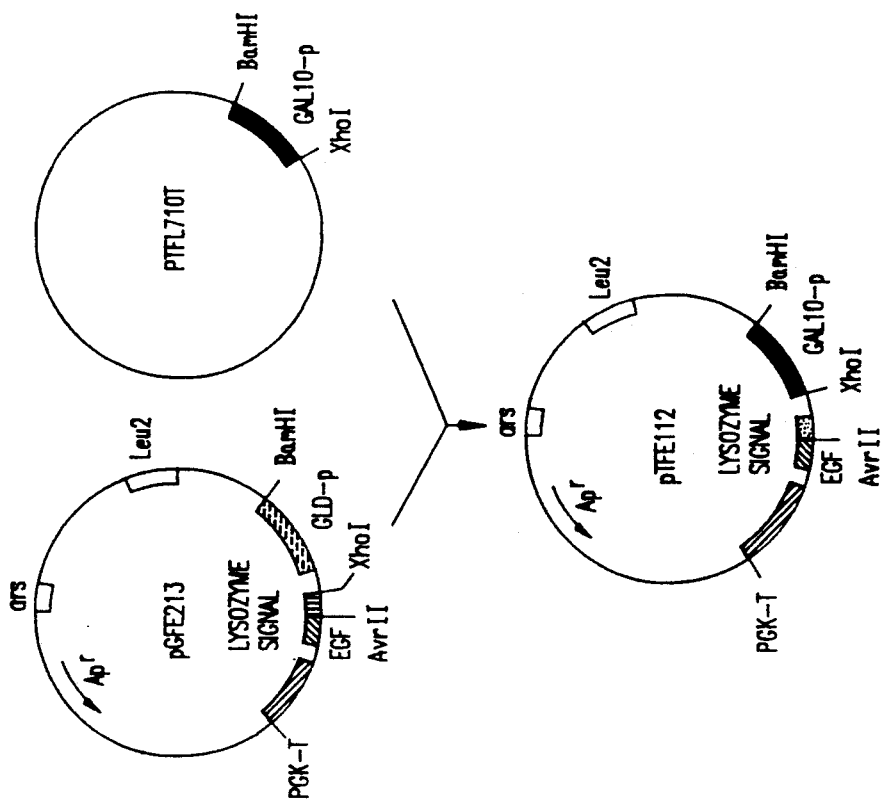
FIG. 22 illustrates a construction scheme of an expression vector pTFE112.

The expression vector pTFE112 was prepared by inserting a 790 bp BamHIXhoI DNA fragment [Gal 10 promoter (indicated as GAL10p)] obtained from pTFL 710T in Reference Example 3 into the BamHI-XhoI site of an expression vector pGFE213 [GLD promoter (indicated as GLDp)] obtained in Reference Example 4 in a correct orientation (FIG. 22).

REFERENCE EXAMPLE 18

Preparation of Rat C-Kinase α Gene

An animal cell expression vector pTB755 (European Patent Publication EP-A-251244, Example 5) which contained a cDNA encoding rat C-kinase α was digested with EcoRI to prepared a 3.3 kbp DNA fragment containing a PKCα gene region, and the fragment was inserted into an EcoRI-digested pUC18 (Takara Shuzo). The recombinant DNA was digested with McoI and PstI or with PstI and StuI to give a 140 bp NcoI-PstI fragment or a 2.0 kbp PstI-StuI fragment. An adaptor was added to the NcoI site of the former fragment with T4 DNA ligase to give a 150 bp AvrII-PstI DNA fragment.

Figure 23:
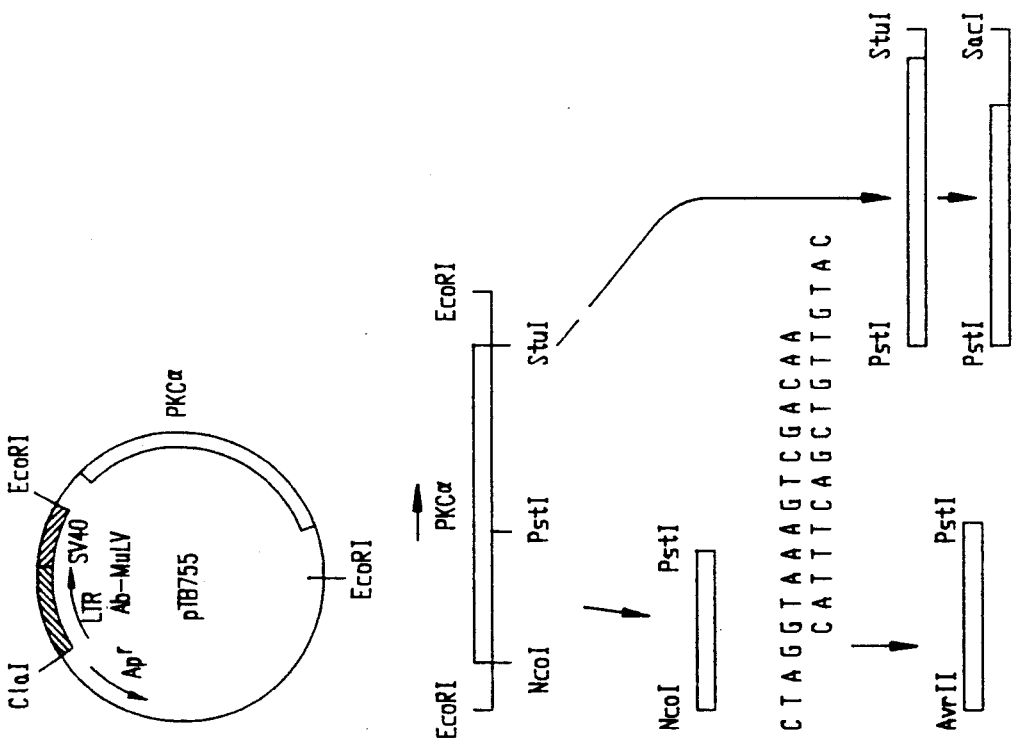
FIGS. 23 to 25 show construction steps of several plasmids.

An SacI linker of octamer pCGAGCTCG(NEB) was added to the StuI site of the latter fragment with T4 DNA ligase, and the resulting fragment was digested with SacI to give a 2.0 kbp PstI-SacI fragment (FIG. 23).

REFERENCE EXAMPLE 19

Construction of Expression Plasmid-1

Figure 24:
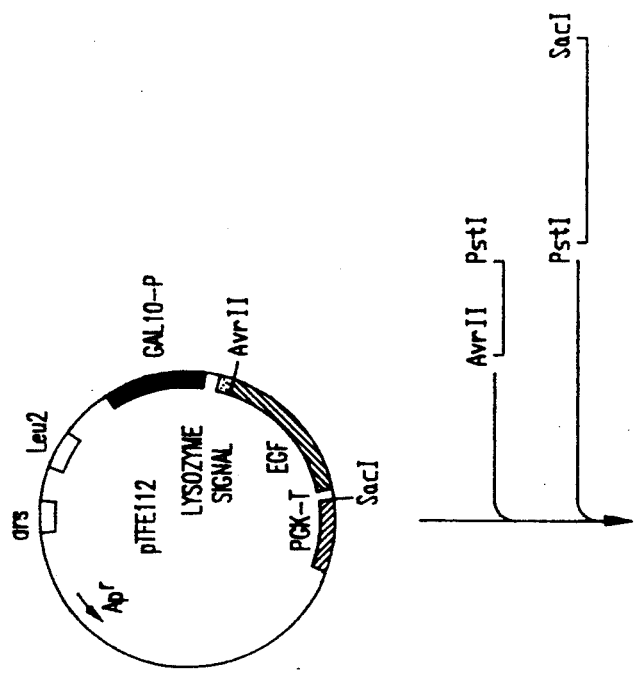

The yeast expression plasmid pTFE112 obtained in Reference Example 17 was digested with restriction enzymes AvrII and SacI to give a 9.6 kbp DNA fragment. The 150 bp fragment and the 2.0 kbp fragment obtained in Reference Example 18 were inserted into the 9.6 kbp fragment to construct an expression plasmid pTFE755 (FIG. 24).

REFERENCE EXAMPLE 20

Construction of Expression Plasmid-2

Figure 25:
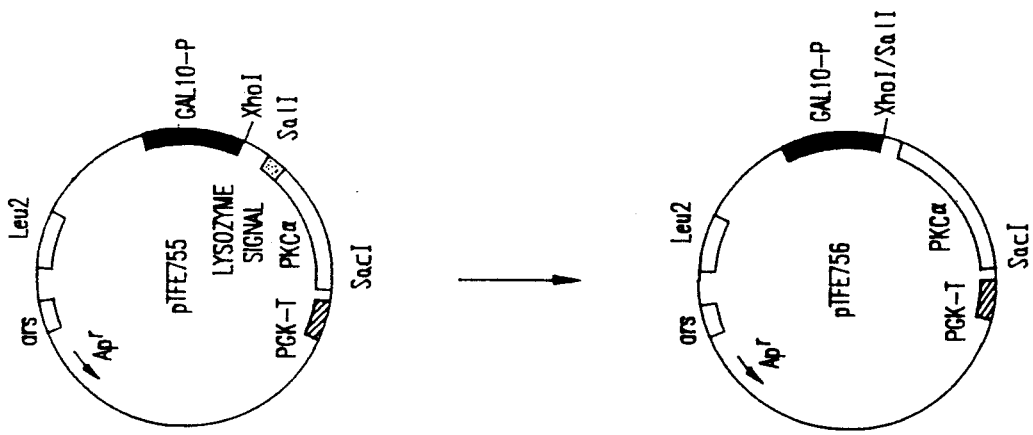

The plasmid pTFE755 obtained in Reference Example 19 was digested with SalI and SacI, and the obtained 2.2 kbp fragment was inserted into the XhoI-SacI site of pTFE112 to construct an expression plasmid pTFE756 (FIG. 25).

EXAMPLE 14

Preparation and Cultivation of Yeast Transformant and Expression of PKCα Protein Yeast Saccharomyces cerevisiae NA74-3A($p^-$) was transformed with plasmids pTFE755 and pTFE756 obtained in Reference Examples 19 and 20 to give transformants Saccharomyces cerevisiae NA74-3A($p^-$)/pTFE755 and Saccharomyces cerevisiae NA74-3A($p^-$)/pTFE756, respectively.

Each of the yeast transformants was cultivated at 30° C. for 3 days with shaking in 5 ml of a culture broth [3 g of $K_2HPO_4$, 50 g of glucose, 4 g of L-asparagine, 100 mg of L-histidine, 0.1 mg of KI, 500 mg of $MgSO_4 \cdot 7H_2O$, 330 mg of $CaCl_2 \cdot 2H_2O$, 0.4 mg of $CuSO_4 \cdot 5H_2O$, 2.5 mg of $FeSO_4 \cdot 7H_2O$, 0.4 mg of $MnSO_4 \cdot 4H_2O$, 0.2 mg of $(NH_4)_3PO_4 \cdot 12MoO_3 \cdot 3H_2O$, 3.1 mg of $ZuSO_4 \cdot 7H_2O$, 10 mg of inositol, 0.2 mg of thiamine, 0.2 mg of pyridoxine, 0.2 mg of Ca-pantothenate, 0.2 mg of niacin and 0.002 mg of biotin, per 1], and 0.5 ml of the culture was transferred to 4.5 ml of another culture broth having the same composition as above and cultivated at 30° C. for 1 day. Then, 2 ml of the culture was transferred to 18 ml of a fresh medium [400 mg of $K_2HPO_4$, 80 g of sucrose, 5 g of L-asparagine, 300 mg of L-histidine, 2.0 g of KCl, 0.1 mg of KI, 650 mg of $MgSO_4 \cdot 7H_2O$, 429 mg of $CaCl_2 \cdot 2H_2O$, 10 g of galactose, 25 mM of Trismaleic acid (pH 6.5), 0.4 mg of $CuSO_4 \cdot 5H_2O$, 2.5 mg of FeSO$_4$·7H$_2$O, 0.4 mg of MnSO$_4$·4H$_2$O, 0.2 mg of (NH$_4$)$_3$PO$_4$·12MoO$_3$·3 H$_2$O, 3.1 mg of ZnSO$_4$·7H$_2$O, 10 mg of inositol, 0.2 mg of thiamine, 0.2 mg of pyridoxine, 4.0 mg of Ca-pantothenate, 4.0 mg of niacin and 0.040 mg of biotin, per 1] and cultivated at 30° C. with shaking. After 72 hours, the culture was sampled and centrifuged (10,000×g, 10 minutes) for separation into a supernatant and cells.

The cells (200 mg, wet cell weight) were suspended in an extraction buffer [0.1% Tween 20, 7.5M urea, 15 mM EDTA (ethylenediaminetetraacetic acid), 2 mM PMSF (phenylmethylsulfonyl fluoride), 0.2 mM APMSF (paraaminophenylmethanesulfonyl fluoride hydrochloride), 5 mM EGTA (ethylaneglycol-bis-β-aminoethyl ether)-N,N,N',N'-tetraacetic acid), 0.1M phosphate buffer, pH7.2] and disrupted with 1 g of glass beads by Vortex mixer at 4° C. for 30 minutes, and then centrifuged (12,000 rpm, 10 minutes) to recover a supernatant. An equal volume of an SDS-gel sample buffer [V. K. Laemmli et al., Nature, 227, 680 (1970)] was added to the supernatant, and the resulting mixture was heated at 100° C. for 10 minutes to solubilize proteins. The solubilized proteins were fractionated by SDS-polyacrylamide gel electrophoresis and then transferred onto a nitrocellulose filter by the known Western blotting method [H. Towbin et al., Proc. Natl. Acad. Sci. USA, 76, 4350(1979)]. The screening of the PKCα protein by a known anti-PKCα monoclonal antibody (M. C. Clone et al., Amersham) revealed that a PKCα protein having a well identical molecular weight was expressed.

EXAMPLE 15

Assay for PKC Activity

The cells (200 mg, wet cell weight) obtained by cultivation according to the method described in Example 14 were suspended in 500 μl of 0.1M Tris-hydrochloric acid buffer (pH 7.5) containing 20% glycerol, 1 mM APMSF and 5 mM EGTA, disrupted with 1 g of glass beads, and then centrifuged (12,000 rpm, 10 minutes) to recover a supernatant. The assay for protein kinase C according to the method of Kikkawa et al. [U. Kikkawa et al., J. Biol. Chem., 257, 13341(1982)] proved that the supernatant showed protein kinase activity against histon type I dependent upon phorbol ester, phospholipid and Ca$^{++}$. The control not expressing the PKCα protein did not show any protein kinase activity.

The following microorganisms which are disclosed in the Examples and Reference Examples have been deposited in the Institute for Fermentation (IFO), Osaka, Japan and in the Fermentation Research Institute, Agency of Industrial Science and Technology (FRI), Japan under the Budapest Treaty.

| Microorganism | IFO | FRI(FERM) |
|---|---|---|
| *Saccharomyces cerevisiae* | | |
| 1. NA74-3A | 10430 | BP-1947 (P-9691) |
| 2. NA74-3A(p$^-$) | 10431 | BP-1948 (P-9692) |
| 3. NA74-3A/pTFL710T | 10432 | BP-2090 (P-9693) |
| 4. NA74-3A(p$^-$)/pTFL710T | 10433 | BP-2091 (P-9694) |
| 5. K33-7B(p$^-$) | 10457 | BP-2092 |
| 6. NA87-11A(p$^-$) | 10458 | BP-2093 |
| 7. NA74-3A(p$^-$)/pPFL725T | 10459 | BP-2094 |
| 8. NA74-3A(p$^-$)/pGFE213 | 10460 | BP-2095 |
| 9. NAX-50D(p$^-$)/pTFL710T | 10461 | BP-2096 |
| 10. AH22R$^-$/pGFL735 | 10227 | BP-1346 |
| 11. AH22R$^-$/pGEL125 | 10211 | BP-1345 (P-8806) |
| 12. AH22R$^-$/pGLD P31-RcT | 10206 | BP-1059 |
| 13. NA74-3A(p$^-$)/pHSD100 | 10436 | BP-1955 |
| 14. NA74-3A(p$^-$)/pHSD103S | 10437 | BP-1956 |
| 15. NA74-3A(p$^-$)/pHSD104S | 10438 | BP-1957 |
| 16. NA74-3A(p$^-$)/pHSD105S | 10439 | BP-1958 |
| 17. NA74-3A(p$^-$)/pHTI501 | 10440 | BP-1961 |
| 18. NA74-3A(p$^-$)/pHTI511 | 10441 | BP-1962 |
| 19. NA74-3A(p$^-$)/pTFE755 | 10442 | BP-1976 |
| 20. NA74-3A(p$^-$)/pTFE756 | 10443 | BP-1977 |
| *Escherichia coli* | | |
| 21. DH1/pHSD BJ-1 | 14730 | BP-1784 |

The following references, which are referred to for their disclosures at various points in this application, are incorporated herein by reference Biochem. Biophys, Res Commun., 145, 712(1987)
Kobo no Kaibo, Kodensha Scientific, p. 137-147 1981.
Mol. Cell. Biol., 5, 248 (1985)
Proc. Natl. Acad. Sci. U.S.A. 80, 1(1983)
Mol. Cell. Biol., 4, 771(1984)
J. Bacteriol. 153, 163 (1983)
Proc. Natl. Acea. Sci. U.S.A. 75, 1927 (1978).
Amper. J. Bot. 30, 206 (1943).
J. Bacteriol 113, 727 (1973).
Biochem. Biophys. Res. Commun. 145, 712 (1987)
Pro. Natl. Acad. Sci. U.S.A. 72, 1371 (1975)
Nucl. Acids. Res., 7, 1513 (1979)
Chem. Pharm. Bull. 34, 2202 (1986)
Pro. Natl. Acad. Sci. U.S.A. 69, 2110 (1972)
Pro. Natl. Acad. Sci. U.S.A. 77, 5759 (1980)
Tetrahedron Letters 22, 1859 (1981)
Mol. Cell. Biol. 4, 1440 (1984)
J. Takeda Res. Lab. 45, 136 (1986)
Japanese Patent Unexamined Publication 88881/1986

We claim:

1. Respiratory-deficient yeast excluding *Saccharomyces cerevisiae* AH22R$^-$, said respiratory-deficient yeast being transformed with a DNA containing a gene encoding a protein foreign to yeast and capable of expressing a foreign DNA, wherein the yeast is *Saccharomyces cerevisiae* NA74-3A(p$^-$), *Saccharomyces cerevisiae* K33-7B(p$^-$), *Saccharomyces cerevisiae* NAX-50D(p$^-$), *Saccharomyces cerevisiae* NA74-3A(p$^-$)/pTFL710T, *Saccharomyces cerevisiae* NA74-3A(p$^-$)/pPFL725T, *Saccharomyces cerevisiae* NA74-3A(p$^-$)/pGFE313, or *Saccharomyces cerevisiae* NAX-50D(p$^-$)/pTFL710T.

2. Yeast as claimed in claim 1, wherein the gene is a human lysozyme gene or a human EGF gene.

3. Yeast as claimed in claim 1, wherein a promoter used for expression of the gene is a promoter of a glyceraldehyde-3-phosphate dehydrogenase gene (GLD), acid phosphatase gene (PHO5) or uridine-galactose diphosphate-4-spimerase gene (Ga110).

4. Yeast as claimed in claim 1, wherein the gene is a gene encoding at least one animal enzyme, growth factor, hormone, lymphokine or viral protein.

5. Yeast as claimed in claim 1, wherein the gene is a gene encoding at least one of human lysozyme, protein disulfide isomerase, protein kinase C, huma EGF, basic FGF, nerve growth factor, growth hormone, insulin, interferon α, interferon β, interferon γ, interleukin 2, hepatitis B virus surface antigen, HTLV-1 or lymphotoxin.

6. A method for preparing a protein foreign to yeast, which comprise culturing respiratory-deficient yeast according to claim 1, said respiratory-deficient yeast being transformed with a DNA containing a gene encoding a protein foreign to yeast, and producing and accumulating the protein in a culture.

7. A method for preparing a protein as claimed in claim 6, wherein the protein is human lysozyme or human EGF.

* * * * *

UNITED STATES PATENT AND TRADEMARK OFFICE
CERTIFICATE OF CORRECTION

PATENT NO. : 5,182,195
DATED : January 26, 1993
INVENTOR(S) : Nakahama et al.

It is certified that error appears in the above-identified patent and that said Letters Patent is hereby corrected as shown below:

At column 24, line 42, change "NA74-3A($\rho^-$)pGFE313" to --NA74-3A($\rho^-$)/pGFE213 --.

Signed and Sealed this

Twenty-eighth Day of December, 1993

Attest:

BRUCE LEHMAN

Attesting Officer       Commissioner of Patents and Trademarks